United States Patent
Yue et al.

(10) Patent No.: US 6,245,526 B1
(45) Date of Patent: Jun. 12, 2001

(54) LIPID METABOLISM TRANSCRIPTION FACTOR

(75) Inventors: Henry Yue, Sunnyvale; Matthew R. Kaser, Castro Valley; Mariah R. Baughn, San Leandro, all of CA (US)

(73) Assignee: Incyte Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 09/318,978

(22) Filed: May 26, 1999

(51) Int. Cl.[7] ............................. C12P 21/06; C12Q 1/68; C07H 17/00
(52) U.S. Cl. ..................... 435/69.1; 435/325; 435/252.3; 435/320.16; 536/23.1
(58) Field of Search ........................... 435/69.1, 6, 252.3, 435/320.1, 325; 536/23.1

(56) References Cited

PUBLICATIONS

Moncur, J.T., et al, The "Spot 14" gene resides on the telomeric end of the 11q13 amplicon and is expressed in lipogenic breast cancers: Implications for control of tumor metabolism, *Proc. Natl. Acad. Sci. USA*, 95:6989–6994, (Jun. 1998).

Cunnigham, BA, et al., Abstract, "Spot 14" protein: a metabolic integrator in normal and neoplastic cells, *Thyroid*, 8(9):815–25, (Sep. 1998).

Liaw, C.W., et al., Characterization of a Thyroid Hormone–responsive Gene from Rat, *Journal of Biological Chemistry*, 259 (11):7253–7260, (Jun. 1984).

Brown, Susan, B., et al., "Spot 14" Protein Functions at the Pretranslational Level in the Regulation of Hepatic metabolism by Thyroid Hormone and Glucose, *Journal of Biological Chemistry*, 272(4):2163–2166, (Jan. 1997).

Conway, G., A novel gene expressed during zebrafish gastrulation identified by differential RNA display, *Mechanism of Development*, 52:383–391, (1995).

Fink, R. D., et al., Apical Membrane Turnover is Accelerated Near Cell—Cell Contacts in an Embryonic Epithelium, *Developmental Biology*, 174, 180–189, (1996).

Conway, G., (Direct Submission), GenBank Sequence Database (Accession AAA96952), National Center for Biotechnology Information, National Library of Medicine, Bethesda, Maryland, 20894 (GI 861207).

Grillasca, J.P. et al., (Direct Submission), GenBank Sequence Database (Accession CAA64600), National Center For Biotechnology Information, National Library of Medicine, Bethesda, Maryland, 20894 (GI 1171574).

*Primary Examiner*—Karen Cochrane Carlson
(74) *Attorney, Agent, or Firm*—Incyte Genomics, Inc.; Lynn E. Murry

(57) ABSTRACT

The invention provides a mammalian nucleic acid sequence and fragments thereof. It also provides for the use of these nucleic acid sequences in a model system for the characterization, diagnosis, evaluation, treatment, or prevention of conditions, diseases and disorders associated with expression of the mammalian nucleic acid sequence. The invention additionally provides expression vectors and host cells for the production of the protein encoded by the mammalian nucleic acid sequence.

13 Claims, 8 Drawing Sheets

```
            11          20          29          38    47          56
5' GGGCC TTT TAT CTC GGT GCT GCC GGG GGA GGC GGG AGG AGA CAC CAG GGG TGG 65          74          83          92   101         110
   CCC TGA GCG CCG GCG ACA CCT TTC CTG GAC TAT AAA TTG AGC ACC TGG GAT GGG 119         128         137         146   155         164
   TAG GGG GCC AAC GCA GTC CGC ACC GCC GTC CGC AGT CAC AGT CCA ACT GAC CGC 173         182         191         200   209         218
   AGC AGC GCC CTT GCG TAC AGC CGC TTG CAG CGA GAA CAC TGA ATT GCC AAC GAG 227         236         245         254   263         272
   CAG GAG AGT CTC AAG GCG CAA GAG GCC AGG GCT CGA CCC ACA GAG CAC CCT 281         290         299         308   317         326
   CAG CCA TCG CGA GTT TCC GGG CGC CAA AGC CAG GAG AAG CCG CCC ATC CCG CAG 335         344         353         362   371         380
   GGC CGG TCT GCC AGC GAG ACG AGA GTT GGC GAG GGC GGA GGA GTG CCG GGA ATC
```

FIGURE 1A

```
         389         398         407         416         425         434
CCG CCA CAC CGG CTA TAG CCA GGC CCC CAG CGC GGG CCT TGG AGA GCG CGT GAA 443         452         461         470         479         488
GGC GGG CAT CCC CTT GAC CCC GCC CCG GCC GAC CAT CCC GCC CGT GCC CCT GCG TCC CTG CGC 497         506         515         524         533         542
TCC AAC GTC CGC GCG ACC ATG CAA ATC TGC GAC ACC TAC AAC CAG AAG
  S   N   V   R   A   T   M   M   Q   I   C   D   T   Y   N   Q   K 551         560         569         578         587         596
CAC TCG CTC TTT AAC GCC ATG AGC CGC TTC ATT GGC GCC GTG AAC AAC ATG GAC
  H   S   L   F   N   A   M   S   R   F   I   G   A   V   N   N   M   D 605         614         623         632         641         650
CAG ACG GTG ATG GTG CCC AGC TTG CTG CGC GAC CCC GTG GCT GAC CCC GGG
  Q   T   V   M   V   P   S   L   L   R   D   P   L   A   D   P   G 659         668         677         686         695         704
AAC GAT GTT GGC GTG GAG GTA GGC AGT GGC GGC TGC CTG GAG GAG
  N   D   V   G   V   E   V   G   S   G   G   C   L   E   E 713         722         731         740         749         758
CGC ACG CCC CCA GTC CCC GAC TCG GGA AGC GCC AAT GGC AGC TTT TTC GCG CCC
  R   T   P   P   V   P   D   S   G   S   A   N   G   S   F   F   A   P
```

FIGURE 1B

```
      767         776         785         794         803         812
TCT CGG GAC ATG TAC AGC CAC TAC GTG CTT CTC AAG TCC ATC CGC AAC GAC ATC 821         830         839         848         857         866
GAG TGG GGG GTC CTG CAC CAG CCG CCT CCA CCG GCT GGG AGC GAG GAG GGC AGT 875         884         893         902         911         920
GCC TGG AAG TCC AAG GAC ATC CTG GTG GAC CTG GGC CAC TTG GAG GGT GCG GAC 929         938         947         956         965         974
GCC GGC GAA GAA GAC CTG GAA CAG TTC CAC TAC CAC CTG CGC GGG CTG CAC 983         992        1001        1010        1019        1028
ACT GTG CTC TCG AAA CTC ACG CGC AAA GCC AAC ATC CTC ACT AAC AGA TAC AAG 1037        1046        1055        1064        1073        1082
CAG GAG ATC GGC TTC AAT TGG GGC CAC TGA GGC GTG GCG CCC GTG GCT GCC
 Q   E   I   G   F   N   W   G   H 1091        1100        1109        1118        1127        1136
CAG CAC CTT CTT CGA CCC ATC TCA CCC TCT CTC ATT CCT CAA AGC TTT TTT TTT
```

FIGURE 1C

```
          1145                1154           1163           1172           1181           1190
TTT TCC TGG CTG GGG GGC GGG AAG GGC AGA CTG CAA ACT GGG GGG CTG CGT ACG 1199                1208           1217           1226           1235           1244
TGC AGG AGG CGC GGT GGG GCT GCG TGG AGG AGG GGG CCA CGT GTG AGA GAG AAG 1253                1262           1271           1280           1289           1298
AAA ATG GTG GCC GGA GAT GGG AGG GCC CAA GGA ACC TCC TGG GAG GGG GCC TGC 1307                1316           1325           1334           1343           1352
ATT CTA TGT TGG TGG GAA TGG GAC TGG GCT GAC GCC CTG CAT TCA GCC TGT GCC 1361                1370           1379           1388           1397           1406
TTT CCT GGG GTT TCT TTT CTG TTC TTT TCG GAG GAG AGG GCC CGA GAA GGG GCC 1415                1424           1433           1442           1451           1460
ATA CCA GGG CGG GGC GCT GGG TTG CCA CAC TTG GGA AAG CAG CCC GGA GCT GGG 1469                1478           1487           1496           1505           1514
TGC TGG GGA AGG CGG GGC GCG TAG CCT CCC GCC GCC CTG CGG TTG GGC CGG TGG
```

FIGURE 1D

```
      1523          1532          1541          1550          1559          1568
AGG CCC AGG CGT TGC TAG GAT TGC ATC AGT TTT CCT GTT TGC ACT ATT TCT TTT 1577          1586          1595          1604          1613          1622
TGT AAC ATT GGC CCT GTG TGA AGT ATT TCG AAT CTC CTC CTT GCT CTG AAA CTT 1631          1640          1649          1658          1667          1676
CAG CGA TTC CAT TGT GAT AAG CGC ACA AAC AGC ACT GTC TGT CGG TAA TCG GTA 1685          1694          1703          1712          1721          1730
CTA CTT TAT TAA TGA TTT TCT GTT ACA CTG TAT AGT AGT CCT ATG GCA CCC CCA 1739          1748          1757          1766          1775          1784
CCC CAT CCC TTT CGT GCC ACT CCC GTC CCC ACC CCC ACC CCA GTG TGT ATA AGC 1793          1802          1811          1820          1829          1838
TGG CAT TTC GCC AGC TTG TAC GTA GCT TGC CAC TCA GTG AAA ATA ATA ACA TTA
```

FIGURE 1E

```
     1847           1856           1865           1874           1883           1892
TTA TGA GAA AGT GGA CTT AAC CGA AAT GGA ACC AAC TGA CAT TCT ATC GTG TTG 1901           1910           1919           1928           1937           1946
TAC ATA GAA TGA TGA AGG GTT CCA CTG TTG TAT GTC TTA AAT TTA TTT AAA 1955           1964           1973           1982           1991           2000
ACT TTT TTT AAT CCA GAT GTA GAC TAT ATT CTA AAA AAT AAA AAA GCA AAT GTG 2009           2018           2027           2036           2045           2054
TCA ACT AAA TTG GAC AAG CGT CTG CTC ATT AAT CTG CCA ATG AAT GGT TTC 2063           2072           2081           2090
GTC ATT AAA TAA AAA TCA ATT TAA TTG ATT TAC TAG CA 3'
```

```
118 GSAWKSKDILVDLGHLEGADAGEEDLEQQF         5595953
 88 EDQRRKKDTSAS-EPVRTEEESDMDLEQLL         GI 861207
 90 SEA--ENDAAETEEAEEDRISEELDLEAQF         GI 1171574

148 HYHLRGLHTVLSKLTRKANILTNRYKQEIG         5595953
117 QFHLKGLHGVLSQLTSQANNLTNRYKQEIG         GI 861207
118 HLHFCSLHHILTHLTRRKAQEVTRKYQE--         GI 1171574

178 FGNWGH                                 5595953
147 ISGWGQ                                 GI 861207
145 MTGQVL                                 GI 1171574
```

FIGURE 2B

LIPID METABOLISM TRANSCRIPTION FACTOR

FIELD OF THE INVENTION

This invention relates to nucleic acid and amino acid sequences of a new mammalian protein and to the use of these sequences in the characterization, diagnosis, prevention, and treatment of cell proliferative and lipid disorders.

BACKGROUND OF THE INVENTION

Phylogenetic relationships among organisms have been demonstrated many times, and studies from a diversity of prokaryotic and eukaryotic organisms suggest a more or less gradual evolution of biochemical and physiological mechanisms and metabolic pathways. Despite different evolutionary pressures, proteins that regulate the cell cycle in yeast, nematode, fly, rat, and man have common chemical or structural features and modulate the same general cellular activity. Comparisons of human gene sequences with those from other organisms where the structure and/or function may be known allow researchers to draw analogies and to develop model systems for testing hypotheses. These model systems are of great importance in developing and testing diagnostic and therapeutic agents for human conditions, diseases and disorders.

Fatty acids are required for phospholipid, glycolipid, hormone, and intracellular messenger formation; to anchor proteins to membranes; and as fuel molecules. Most cells can synthesize fatty acids from acetate substrates, though many mammalian cells also obtain fatty acids by hydrolysis of triglycerides. Synthesis of phospholipids primarily occurs on the surface of the smooth endoplasmic reticulum. Although most cells constitutively form fatty acids, the level of synthesis varies with the needs of the cell. During phases of rapid cell division, membrane formation requires enhanced production of phospholipids. Animals that have fasted and are then fed high-carbohydrate, low-fat diets show marked increases in the amount and activity of enzymes responsible for fatty acid synthesis. Increased synthesis of long chain fatty acids also occurs in multiple common neoplasms, including those arising in the breast, prostate, ovary, colon, and endometrium. Overexpression of fatty acid synthase (FAS), a major enzyme of fatty acid biosynthesis, is a marker for poor prognosis in breast tumors and has been shown to be important for tumor growth (Moncur et al. (1997) Proc. Natl. Acad. Sci. USA 95:6989–6994).

The transcriptional regulation of enzymes involved in fatty acid synthesis is associated with Spot 14 (S14) protein. S14 is a small, acidic nuclear protein with a carboxy-terminal "zipper" domain involved in homodimer formation. It is expressed in tissues that produce lipids for use as metabolic fuels, such as lactating mammary tissue, white and brown adipose tissue, and liver. The expression of S14 is increased in response to insulin, dietary carbohydrates, glucose, and thyroid hormone and reduced in response to glucagon, fasting, and in diabetes mellitus. Expression of antisense oligonucleotides has shown S14 induces tissue-specific expression of several lipogenic enzymes including FAS and ATP citrate-lyase. The S14 gene is located on chromosome 11 at position q13.5, a chromosoinal region amplified in approximately 20% of breast cancers, and is expressed in several breast cancer-derived cell lines and in a majority of primary breast tumors (Cunningham et al. (1998) Thyroid 8:815–825; Liaw and Towle (1984) J. Biol. Chem. 259:7253–7260; Brown et al. (1997) J. Biol. Chem. 272:2163–2166; and Moncur, supra).

A zebrafish gastrulation protein, G12, shares features with S14 including acidic pI (~4.9) and nearly identical size (~17 kDa). The sequence similarity between the two proteins is strongest at the carboxy terminus, including the zipper domain. G12 is expressed in an outer, enveloping layer of cells (EVL), analogous to the mammalian trophectoderm, during a period in gastrulation in which the EVL layer expands to cover the developing, embryonic deep cell layer. During this stage, apical membrane turnover in the EVL increases and raises the requirement for phospholipids used in plasma membranes (Conway (1995) Mech. Dev. 52:383–391; Fink and Cooper (1996) Dev. Biol. 174:180–189).

The discovery of a polynucleotide encoding a new mammalian protein satisfies a need in the art by providing new compositions which are useful in the characterization, diagnosis, prevention, and treatment of cell proliferative and lipid disorders.

SUMMARY OF THE INVENTION

The invention is based on the discovery of a polynucleotide encoding a mammalian protein (LMTF) which satisfies a need in the art by providing new compositions useful in the characterization, diagnosis, prevention, and treatment of cell proliferative and lipid disorders.

The invention provides an isolated and purified mammalian polynucleotide comprising the nucleic acid sequence of SEQ ID NO:1 or a fragment thereof. The invention also provides fragments homologous to the mammalian polynucleotide from rat, mouse, and monkey.

The invention further provides an isolated and purified polynucleotide or a fragment thereof which hybridizes under high stringency conditions to the polynucleotide of SEQ ID NO:1. The invention also provides an isolated and purified polynucleotide which is complementary to the polynucleotide of SEQ ID NO:1. In one aspect, a single stranded complementary RNA or DNA molecule is used as a probe which hybridizes under high stringency conditions to the mammalian polynucleotide or a fragment thereof.

The invention further provides a method for detecting a polynucleotide in a sample containing nucleic acids, the method comprising the steps of: (a) hybridizing a probe to at least one of the nucleic acids of the sample, thereby forming a hybridization complex; and (b) detecting the hybridization complex, wherein the presence of the hybridization complex correlates with the presence of a polynucleotide in the sample. In one aspect, the method further comprises amplifying the polynucleotide prior to hybridization. The polynucleotide or fragment thereof may comprise an element or target on a microarray. The invention also provides a method for screening a library of molecules for specific binding to a polynucleotide or a fragment thereof, the method comprising providing a library of molecules, combining the polynucleotide of claim 1 with a plurality of molecules under conditions which allow specific binding, and detecting binding of the polynucleotide to each of a plurality of molecules, thereby identifying at least one molecule which specifically binds the polynucleotide. Such molecules are potential regulators of polynucleotide function.

The invention also provides an expression vector containing at least a fragment of the polynucleotide of SEQ ID NO:1. In another aspect, the expression vector is contained within a host cell. The invention further provides a method for producing a polypeptide, the method comprising the steps of culturing the host cell for expression of the polypeptide and recovering the polypeptide from the host cell culture. The invention also provides an isolated and purified polypeptide comprising the amino acid sequence of SEQ ID NO:2 or a portion thereof. Additionally, the invention provides a pharmaceutical composition comprising a substantially purified polypeptide having the sequence of SEQ ID NO:2 or a portion thereof in conjunction with a pharmaceutical carrier.

The invention further provides a method for using a portion of the polypeptide to produce antibodies. The invention also provides a method for using a polypeptide or a portion thereof to screen for molecules which specifically bind the polypeptide, the method comprising the steps of combining the polypeptide or a portion thereof with a library of molecules under conditions which allow complex formation and detecting complex formation, wherein the presence of the complex identifies a molecule which specifically binds the polypeptide. In one aspect, a molecule identified using the method increases the activity of the polypeptide. In another aspect, a molecule identified using the method decreases the activity of the polypeptide.

BRIEF DESCRIPTION OF THE FIGURES AND TABLE

FIGS. 1A, 1B, 1C, 1D, 1E, and 1F show the nucleic acid sequence (SEQ ID NO:1) encoding the amino acid sequence (SEQ ID NO:2) of the mammalian protein. The alignment was produced using MACDNASIS PRO software (Hitachi Software Engineering, South San Francisco Calif.).

FIGS. 2A and 2B show the chemical and structural similarity between SEQ ID NO:2, G12 (GI 861207; SEQ ID NO:26) and Spot14 (GI 1171574; SEQ ID NO:27), produced using the multisequence alignment program of LASERGENE software (DNASTAR, Madison Wis.). The amino acids of SEQ ID NO:2, from residue 45 to residue 59, may be used for antibody production.

Table 1 shows the ESTs from human, rat, mouse, and monkey which have homology with SEQ ID NO:1 and includes their nucleotide length, biological source, region of overlap with SEQ ID NO:1, and percent identity with SEQ ID NO:1.

DESCRIPTION OF THE INVENTION

It is understood that this invention is not limited to the particular machines, materials and methods described. It is also to be understood that the terminology used herein is for the purpose of describing particular embodiments only and is not intended to limit the scope of the present invention which will be limited only by the appended claims. As used herein, the singular forms "a," "an," and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"LMTF" refers to a substantially purified protein obtained from any mammalian species, including murine, bovine, ovine, porcine, simian, and preferably the human species, and from any source, whether natural, synthetic, semi-synthetic, or recombinant.

"Agents, molecules, or compounds" are used substantially interchangably and refer to that which interacts with, specifically binds to, or modifies the polynucleotides and proteins of the invention; and may be composed of at least one of the following: nucleic acids, proteins, carbohydrates, fats, lipids, organic and inorganic substances.

"Biologically active" refers to a protein having structural, immunological, regulatory, or chemical functions of a naturally occurring, recombinant or synthetic molecule.

"Complementary" refer to the natural base pairing by hydrogen bonding between purines and pyrimidines. For example, the sequence A-C-G-T forms hydrogen bonds with its complement T-G-C-A or U-G-C-A. Two single-stranded molecules may be considered partially complementary, if only some of the nucleotides bond, or completely complementary, if nearly all of the nucleotides bond. The degree of complementarity between nucleic acid strands affects the efficiency and strength of the hybridization and amplification reactions.

"Derivative" refers to the chemical modification of a polynucleotide or polypeptide sequence. Chemical modifications of a sequence can include replacement of hydrogen by an alkyl, acyl, or amino group or glycosylation, pegylation, or any similar process which retains or enhances biological activity or lifespan of the molecule.

"Fragment" refers to an Incyte clone or any part of a polynucleotide which retains a usable, functional characteristic. Useful fragments include oligonucleotides which may be used in hybridization or amplification technologies or in regulation of replication, transcription or translation.

"Hybridization complex" refers to a complex between two nucleic acid sequences by virtue of the formation of hydrogen bonds between purines and pyrimidines.

"Polynucleotide" refers to a nucleic acid, nucleic acid sequence, oligonucleotide, nucleotide, or any fragment thereof. It may be DNA or RNA of genomic or synthetic origin, double-stranded or single-stranded, and combined with carbohydrate, lipids, protein or other materials to perform a particular activity such as transformation or form a useful composition such as a peptide nucleic acid (PNA).

"Oligonucleotide" is substantially equivalent to the terms amplimer, primer, oligomer, element, target, and probe and is preferably single stranded.

"Polypeptide" refers to an amino acid, amino acid sequence, oligopeptide, peptide, or protein or portions thereof whether naturally occurring or synthetic.

"Portion", as used herein, refers to any part of a protein used for any purpose, but especially for the screening of molecules or compounds which specifically bind to that part or for the production of antibodies.

"Sample" is used in its broadest sense. A sample containing nucleic acids may comprise a bodily fluid; an extract from a cell, chromosome, organelle, or membrane isolated from a cell; genomic DNA, RNA, or cDNA in solution or bound to a substrate; a cell; a tissue; a tissue print; and the like.

Molecules or compounds which "specifically bind" the mammalian polynucleotide or polypeptide may include, nucleic acids, carbohydrates, lipids, proteins, or any other organic or inorganic molecules or their combinations which stabilize, increase, or decrease the activity of the mammalian protein.

"Substantially purified" refers to nucleic acid or amino acid sequences that are removed from their natural environment and are isolated or separated, and are at least about 60% free, preferably about 75% free, and most preferably about 90% free, from other components with which they are naturally associated.

"Substrate" refers to any rigid or semi-rigid support to which polynucleotides or polypeptides are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

THE INVENTION

The invention is based on the discovery of a new mammalian polynucleotide which encodes a mammalian protein (LMTF) and the use of the nucleic acid sequence, or fragments thereof, and amino acid sequences, or portions thereof, as compositions in the characterization, diagnosis, treatment, or prevention of cell proliferative and lipid disorders.

Nucleic acids encoding the mammalian protein of the present invention were identified by BLAST using Incyte clone 700145292H1 which was differentially expressed in male rat reproductive tissue. A consensus sequence, SEQ ID NO:1, was assembled from the following overlapping and/or extended nucleic acid fragments found in Incyte Clones 1479946F6, 3241390F6, 1432520R1, 4534217H1, 2191992H1, 1320132T1, 1516707T1, 5595953H1, and 1988906R6; SEQ ID NOs:3–11, respectively. FIGS. 1A, 1B, 1C, 1D, 1E, and 1F show the concensus sequence and translation of SEQ ID NO:1.

In one embodiment, the protein comprising the amino acid sequence of SEQ ID NO:2, LMTF, is 183 amino acids in length and has one potential N-glycosylation site at residue N77; three potential protein kinase C phosphorylation sites at residues S96, T162, and T169; and a potential leucine zipper motif from residue L154 through L168. As shown in FIGS. 2A and 2B, the protein has chemical and structural similarity with zebrafish G12 (GI861207; SEQ ID NO:26) and mouse S14 (GI11171574; SEQ ID NO:27). In particular, LMTF shares 48% identity with G12 protein and 32% identity with S14. LMTF, G12, and S14 are similar in size (20 kDa, 17.5 kDa, and 17 kDa, respectively) and isoelectric point (5.3, 5.0, and 4.8, respectively), as calculated using LASERGENE software (DNASTAR). Furthermore, LMTF, G12, and S14 share conserved leucine residues comprising a zipper motif at residues L154, L161, and L168 in LMTF.

Table 1 shows the nucleic acid fragments from human, rat, mouse, and monkey and their sequence coverage and identity with SEQ ID NO:1. Columns 1 and 2 list the SEQ ID NO and Incyte clone number, respectively, for each nucleic acid fragment. The fragments of SEQ ID NO:1, SEQ ID NOs:3–11, are useful in hybridization or amplification technologies to identify and distinguish between the mammalian protein disclosed herein and similar sequences including SEQ ID NOs:12–25. Column 3 lists the nucleotide length for each fragment. Columns 4 and 5 identify the source organism and Incyte cDNA library from which the fragments were isolated, respectively. Column 6 identifies the range of nucleotide residues in SEQ ID NO:1 over which each fragment shows identity. Column 7 shows the percent sequence identity between each fragment and SEQ ID NO:1 over the nucleotides set forth in column 6.

Northern analysis shows the expression of LMTF in various libraries, particularly in nervous tissues of human, rat, and monkey. Of particular note is the expression of LMTF in conditions associated with cell proliferation, such as cancer and inflammation.

The mammalian fragments comprising SEQ ID NO:12–13 from monkey, SEQ ID NO:14–15 from mouse, and SEQ ID NO:16–25 from rat were identified using either SEQ ID NO:1 or SEQ ID NOs:3–11. These fragments may be used to obtain the full length sequence for a particular species which in turn can be used to produce transgenic animals which mimic human diseases. The fragments are useful in hybridization and amplication technologies to monitor animal toxicological studies, clinical trials, and subject/patient treatment profiles through time.

Characterization and Use of the Invention

In a particular embodiment disclosed herein, mRNA was isolated from mammalian cells and tissues using methods which are well known to those skilled in the art and used to prepare the cDNA libraries. The Incyte clones listed above were isolated from mammalian cDNA libraries. At least one library preparation representative of the invention is described in the EXAMPLES below. The consensus mammalian sequence was chemically and/or electronically assembled from fragments including Incyte clones, extension, and/or shotgun sequences using computer prorams such as the AUTOASSEMBLER application Applied Biosystems, Foster City, Calif.

Methods for sequencing nucleic acids are well known in the art and may be used to practice any of the embodiments of the invention. These methods employ enzymes such as the Klenow fragment of DNA polymerase I, SEQUENASE Taq DNA polymerase, thermostable T7 DNA polymerase (Amersham Pharmacia Biotech, Piscataway N.J.), or combinations of polymerases and proofreading exonucleases such as those found in the ELONGASE amplification system (Life Technologies, Rockville Md.). Preferably, sequence preparation is automated with machines such as the HYDRA microdispenser (Robbins Scientific, Sunnyvale Calif.), MICROLAB 2200 system (Hamilton, Reno Nev.), and the DNA ENGINE thermal cycler (PTC200; MJ Research, Watertown Mass.). Machines used for sequencing include the ABI 3700, 377 or 373 DNA sequencing systems Applied Biosystems, the MEGABACE 1000 DNA sequencing system (Amersham Pharmacia Biotech), and the like. The sequences may be analyzed using a variety of algorithms which are well known in the art and described in Ausubel (1997; *Short Protocols in Molecular Biology*, John Wiley & Sons, New York N.Y., unit 7.7) and Meyers (1995; *Molecular Biology and Biotechnology*, Wiley VCH, New York N.Y., pp. 856–853).

Shotgun sequencing is used to generate more sequence from cloned inserts derived from multiple sources. Shotgun sequencing methods are well known in the art and use thermostable DNA polymerases, heat-labile DNA polymerases, and primers chosen from representative of regions flanking the nucleic acid sequences of interest. Prefinished sequences (incomplete assembled sequences) are inspected for identity using various algorithms or programs well known in the art, CONSED (Gordon (1998) Genome Res. 8:195–202). Contaminating sequences including vector or chimeric sequences or deleted sequences can be removed or restored, respectively, organizing the prefinished sequences into finished sequences.

The sequences of the invention may be extended using various PCR-based methods known in the art. For example, the XL-PCR kit Applied Biosystems, nested primers, and commercially available cDNA or genomic DNA libraries (Life Technologies; Clontech, Palo Alto Calif., respectively) may be used to extend the nucleotide sequence. For all PCR-based methods, primers may be designed using commercially available software, such as OLIGO software Molecular Biology Insights, Cascade Co. to be about 22 to 30 nucleotides in length, to have a GC content of about 50% or more, and to anneal to a target sequence at temperatures of about 68° C. to 72° C. When extending a sequence to recover regulatory elements, it is preferable to use genomic, rather than cDNA libraries.

The polynucleotide sequence of SEQ ID NO:1 and fragments thereof can be used in various hybridization technologies for various purposes. Hybridization probes may be designed or derived from SEQ ID NO:1. Such probes may be made from a highly specific region such as the 5' regulatory region or from a conserved motif, and used in protocols to identify naturally occurring sequences encoding the mammalian protein, allelic variants, or related sequences, and should preferably have at least 50% sequence identity to any of the protein sequences. The hybridization probes of the subject invention may be DNA or RNA and may be derived from the sequence of SEQ ID NO:1 or from genomic sequences including promoters, enhancers, and introns of the mammalian gene. Hybridization or PCR probes may be produced using oligolabeling, nick translation, end-labeling, or PCR amplification in the presence of the labeled nucleotide. A vector containing the nucleic acid sequence may be used to produce an mRNA probe in vitro by addition of an RNA polymerase and labeled nucleotides. These procedures may be conducted using commercially available kits such as those provided by Amersham Pharmacia Biotech.

The stringency of hybridization is determined by G+C content of the probe, salt concentration, and temperature. In particular, stringency can be increased by reducing the concentration of salt or raising the hybridization temperature. In solutions used for some membrane based hybridizations, additions of an organic solvent such as formamide allows the reaction to occur at a lower temperature. Hybridization can be performed at low stringency with buffers, such as 5×SSC with 1% sodium dodecyl sulfate (SDS) at 60° C., which permits the formation of a hybridization complex between nucleotide sequences that contain some mismatches. Subsequent washes are performed at higher stringency with buffers such as 0.2×SSC with 0.1% SDS at either 45° C. (medium stringency) or 68° C. (high stringency). At high stringency, hybridization complexes will remain stable only where the nucleic acid sequences are completely complementary. In some membrane-based hybridizations, perferably 35% or most preferably 50%, formamide can be added to the hybridization solution to reduce the temperature at which hybridization is performed, and background signals can be reduced by the use of other detergents such as Sarkosyl or Triton X-100 and a blocking agent such as salmon sperm DNA. Selection of components and conditions for hybridization are well known to those skilled in the art and are reviewed in Ausubel (supra) and Sambrook et al. (1989) *Molecular Cloning, A Laboratory Manual*, Cold Spring Harbor Press, Plainview N.Y.

Microarrays may be prepared and analyzed using methods known in the art. Oligonucleotides may be used as either probes or targets in a microarray. The microarray can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc. Natl. Acad. Sci. 93:10614–10619; Baldeschweiler et al. (1995) PCT application WO95/251116; Shalon et al. (1995) PCT application WO95/35505; Heller et al. (1997) Proc. Natl. Acad. Sci. 94:2150–2155; and Heller et al. (1997) U.S. Pat. No. 5,605,662.)

Hybridization probes are also useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome DNA libraries.

A multitude of polynucleotide sequences capable of encoding the mammalian protein may be cloned into a vector and used to express the protein, or portions thereof, in host cells. The nucleotide sequence can be engineered by such methods as DNA shuffling (Stemmer and Crameri (1996) U.S. Pat. No. 5,830,721 incorporated by reference herein) and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and 3' untranslated regions) from various sources which have been selected for their efficiency in a particular host. The vector, nucleic acid sequence, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. Sequences may be ligated into the non-essential E1 or E3 region of the viral genome, and the infective virus used to transform and express the protein in host cells. The Rous sarcoma vims enhancer or SV40 or EBV-based vectors may also be used for high-level protein expression Routine cloning, subcloning, and propagation of polynucleotide sequences can be achieved using the multifunctional PBLUESCRIPT vector (Stratagene, La Jolla Calif.) or PSPORT1 plasmid (Life Technologies). Introduction of a polynucleotide sequence into the multiple cloning site of these vectors disrupts the lacZ gene and allows calorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers, such as anthocyanins, green fluorescent protein (GFP), β glucuronidase, luciferase and the like, may be propagated using tissue culture techniques. Visible markers are also used to quantify the amount of protein expressed by the introduced genes. Verification that the host cell contains the desired mammalian polynucleotide is based on DNA-DNA or DNA-RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells which have specific cellular machinery and characteristic mechanisms for post-translational activities (CHO, HEK293, and WI38; American Type Culture Collection (Mamassas Va.) may be chosen to ensure the correct modification and processing of the foreign protein.

Heterologous moieties engineered into a vector for ease of purification include glutathione S-transferase (GST), calmodulin binding peptide (CBP), 6-His, FLAG, c-myc, and the like. GST, CBP, and 6-His are purified using commercially available affinity matrices such as immobilized glutathione, calmodulin, and metal-chelate resins, respectively. FLAG, and c-myc, are purified using commercially available monoclonal and polyclonal antibodies. A proteolytic cleavage site may be located between the desired protein sequence and the heterologous moiety for ease of separation following purification. Methods for recombinant protein expression and purification are discussed in Ausubel (supra, unit 16) and are commercially available.

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional, amino acid is added to the anchored residue using a coupling agent or pre-activated amino acid derivative and the resin is washed. The full length peptide is synthesized by sequential deprotection, coupling of derivitized amino acids, and washing with dichloromethane and/or N, N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1–S20). Automated synthesis may also be carried out on machines such as the ABI 431A Peptide synthesizer Applied Biosystems. A protein or portion thereof may be substantially purified by preparative high performance liquid chromatography and its composition confirmed by amino acid analysis or by sequencing (Creighton (1984) *Proteins Structures and Molecular Properties*, W. H. Freeman, New York N.Y.).

Various hosts including goats, rabbits, rats, mice, humans, and others may be immunized by injection with mammalian protein or any portion thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligonucleotides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et al. (1975) Nature 256:495–497; Kozbor et al. (1985) J. Immunol. Methods 81:31–42; Cote et al. (1983) Proc. Natl. Acad. Sci. 80:2026–2030; and Cole et al. (1984) Mol. Cell Biol. 62:109–120.)

Alternatively, techniques described for the production of single chain antibodies may be adapted, using methods known in the art, to produce epitope-specific single chain antibodies. Antibody fragments which contain specific binding sites for epitopes of the mammalian protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 246:1275–1281.)

The mammalian protein may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols*, Humana Press, Totowa N.J.).

A wide variety of labels and conjugation techniques are known by those skilled in the art and may be used in various nucleic acid, amino acid, and antibody assays. Synthesis of labeled molecules may be achieved using Promega (Madison Wis.) or Amersham Pharmacia Biotech kits for incorporation of a labeled nucleotide such as $^{32}$P-dCTP, Cy3-dCTP or Cy5-dCTP (Ainersham Pharmacia Biotech) or amino acid such as $^{35}$S-methionine (Amersham Pharmacia Biotech). Nucleic acids and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

DIAGNOSTICS

The polynucleotides, fragments, oligonucleotides, complementary RNA and DNA molecules, and PNAs may be used to detect and quantify altered gene expression, absence/presence vs. excess, expression of mRNAs or to monitor mRNA levels during therapeutic intervention. Condition, diseases or disorders associated with altered expression of LMTF include, but are not limited to, a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and a lipid disorder such as fatty liver, cholestasis, carnitine deficiency, carnitine palmitoyltransferase deficiency, myoadenylate deaminase deficiency, hypertriglyceridemia, lipid storage disorders such Fabry's disease, Gaucher's disease, Niemann-Pick's disease, metachromatic leukodystrophy, adrenoleukodystrophy, $GM_2$ gangliosidosis, and ceroid lipofuscinosis, abetalipoproteinemia, Tangier disease, hyperlipoproteinemia, diabetes mellitus, lipodystrophy, lipomatoses, acute panniculitis, disseminated fat necrosis, adiposis dolorosa, lipoid adrenal hyperplasia, minimal change disease, lipomas, hypercholesterolemia, hypercholesterolemia with hypertriglyceridemia, primary hypoalphalipoproteinemia, hypothyroidism, renal disease, liver disease, lecithin:cholesterol acyltransferase deficiency, cerebrotendinous xanthomatosis, sitosterolemia, hypocholesterolemia, Tay-Sachs disease, Sandhoff's disease, hyperlipidemia, hyperlipemia, lipid myopathies, and obesity. The diagnostic assay may use hybridization or amplification technology to compare gene expression in a biological sample from a patient to standard samples in order to detect altered gene expression. Qualitative or quantitative methods for this comparison are well known in the art.

For example, the nucleotide sequence may be labeled by standard methods and added to a biological sample from a patient. After an incubation period in which hybridization complexes form, the sample is washed and the amount of label, or its signal, is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a sequence or a fragment thereof under conditions for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

THERAPEUTICS

Chemical and structural similarity, e.g., in the context of sequences and motifs, exists between regions of the mammalian LMTF, zebrafish G12, and mouse Spot14. In addition, expression is closely associated with nervous tissue and appears to play a role in cell proliferative and inflammatory disorders. In the treatment of conditions associated with increased expression or activity, it is desirable to decrease expression or protein activity. In the treatment of conditions associated with decreased expression or activity, it is desirable to increase expression or protein activity.

In one embodiment, the mammalian protein or a portion or derivative thereof may be administered to a subject to treat or prevent a condition associated with altered expression or activity of the mammalian protein. Examples of such conditions include, but are not limited to, a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and a lipid disorder such as fatty liver, cholestasis, carnitine deficiency, carnitine palmitoyltransferase deficiency, myoadenylate deaminase deficiency, hypertriglyceridemia, lipid storage disorders such Fabry's disease, Gaucher's disease, Niemann-Pick's disease, metachromatic leukodystrophy, adrenoleukodystrophy, $GM_2$ gangliosidosis, and ceroid lipofuscinosis, abetalipoproteinemia, Tangier disease, hyperlipoproteinemia, diabetes mellitus, lipodystrophy, lipomatoses, acute panniculitis, disseminated fat necrosis, adiposis dolorosa, lipoid adrenal hyperplasia, minimal change disease, lipomas, hypercholesterolemia, hypercholesterolemia with hypertriglyceridemia, primary hypoalphalipoproteinemia, hypothyroidism, renal disease, liver disease, lecithin:cholesterol acyltransferase deficiency, cerebrotendinous xanthomatosis, sitosterolemia, hypocholesterolemia, Tay-Sachs disease, Sandhoff's disease, hyperlipidemia, hyperlipemia, lipid myopathies, and obesity.

In another embodiment, a pharmaceutical composition comprising the substantially purified mammalian protein in conjunction with a pharmaceutical carrier may be administered to a subject to treat or prevent a condition associated with altered expression or activity of the mammalian protein including, but not limited to, those provided above.

In a further embodiment, an agonist which modulates the activity of the mammalian protein may be administered to a subject to treat or prevent a condition associated with altered expression or activity of the protein including, but not limited to, those listed above.

In an additional embodiment, a vector capable of expressing the mammalian protein or a portion or derivative thereof may be administered to a subject to treat or prevent a condition associated with altered expression or activity of protein including, but not limited to, those described above.

In yet another embodiment, an antagonist or inhibitor of the mammalian protein may be administered to a subject to treat or prevent a condition associated with altered expression or activity of the protein. In one aspect, an antibody which specifically binds the mammalian protein may be used directly as an antagonist or indirectly as a targeting or delivery mechanism for bringing a pharmaceutical agent to cells or tissue which express the mammalian protein.

In a still further embodiment, a vector expressing the complement of the polynucleotide encoding the mammalian protein may be administered to a subject to treat or prevent a condition associated with altered expression or activity of the protein including, but not limited to, those described above.

Any of the nucleic acids, complementary sequences, vectors, proteins, agonists, antagonists, or antibodies of the invention may be administered in combination with other therapeutic agents. Selection of the agents for use in combination therapy may be made by one of ordinary skill in the art according to conventional pharmaceutical principles. A combination of therapeutic agents may act synergistically to effect prevention or treatment of a particular condition at a lower dosage of each agent.

Gene expression may be modified by designing complementary sequences or antisense molecules (DNA, RNA, or PNA) to the control, 5', or regulatory regions of the gene encoding the mammalian protein. Oligonucleotides designed with reference to the transcription initiation site are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches*, Futura Publishing, Mt. Kisco N.Y., pp. 163–177.) A complementary sequence may also be designed to block translation by preventing binding between ribosomes and mRNA.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio- groups renders the molecule less available to endogenous endonucleases.

The nucleic acid sequence encoding the mammalian protein may be used to screen a library of molecules for specific binding affinity. The assay can be used to screen a library of DNA molecules, RNA molecules, PNAs, peptides, or proteins including transcription factors, enhancers, repressors, and the like which regulate the activity of the nucleic acid sequence in the biological system. The assay involves providing a library of molecules, combining the mammalian nucleic acid sequence or a fragment thereof with the library of molecules under conditions to allow specific binding, and detecting specific binding to identify at least one molecule which specifically binds the nucleic acid sequence.

Similarly the mammalian protein or a portion thereof may be used to screen libraries of molecules in any of a variety of screening assays. The portion of the protein employed in such screening may be free in solution, affixed to an abiotic or biotic substrate (e.g. borne on a cell surface), or located intracellularly. Specific binding between the protein and molecule may be measured. Depending on the kind of library being screened, the assay may be used to identify DNA, RNA, or PNA molecules, agonists, antagonists, antibodies, immunoglobulins, inhibitors, peptides, proteins, drugs and the like, which specifically bind the protein. One method for high throughput screening using very small assay volumes and very small amounts of test compound is described in U.S. Pat. No. 5,876,946, incorporated herein by reference, which screens large numbers of molecules for enzyme inhibition or receptor binding.

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it may be expressed as the ratio, LD50/ED50. Pharmaceutical compositions which exhibit large therapeutic indexes are preferred. The data obtained from cell culture assays and animal studies are used in formulating a range of dosage for human use.

MODEL SYSTEMS

Animal models may be used as bioassays where they exhibit a toxic response similar to that of humans and where exposure conditions are relevant to human exposures. Mammals are the most common models and most toxicity studies are performed on rodents such as rats or mice because of low cost, availability, and abundant reference toxicologic. Inbred rodent strains provide a convenient model for investigation of the physiological consequences of under- or over-expression of genes of interest and for the development of methods for diagnosis and treatment of diseases. A rodent strain inbred to over-express a particular gene may also serve as a convenient source of the protein expressed by that gene.

Toxicology is the study of the effects of agents on living systems. The majority of toxicity studies are performed on rats or mice to help predict the effects of these agents on human health. Observation of qualitative and quantitative changes in physiology, behavior, homeostatic processes, and lethality are used to generate a toxicity profile and to assess the consequences on human health following exposure to the agent.

Toxicological tests measure the effects of a single, repeated, or long-term exposure of a subject to an agent. Agents may be tested for specific endpoints such as cytotoxicity, mutagenicity, carcinogenicity and teratogenicity. Degree of response varies according to the route of exposure (contact, ingestion, injection, or inhalation), age, sex, genetic makeup, and health status of the subject. Toxicokinetic studies trace the absorption, distribution, metabolism, storage, and excretion of the agent in subject tissues, and toxicodynamic studies chart biological responses that are consequences of the presence of the agent in subject tissues.

Genetic toxicology identifies and analyzes the ability of an agent to produce genetic mutations Genotoxic agents usually have common chemical or physical properties that facilitate interaction with nucleic acids and are most harmful when chromosomal aberrations are passed along to progeny. Toxicological studies may identify agents that increase the frequency of structural or functional abnormalities in progeny if administered to either parent before conception, to the mother during pregnancy, or to the developing organism. Mice and rats are most frequently used in these tests because of their short reproductive cycle and their capacity to be raised in numbers sufficient to satisfy statistical requirements.

All toxicology studies on experimental animals involve the preparation of a form of the agent for administration, the selection of the route of administration, and the selection of the species to resemble the species of pharmacological interest. Dose concentrations are varied to investigate a range of dose-related effects which are identified, measured, and related to exposure.

Acute toxicity tests are based on a single administration of the agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Prolonged toxicity tests are based on the repeated administration of the agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic rodents which over-express or under-express a gene of interest may be inbred and used to model human diseases or to test therapeutic or toxic agents. (See, e.g., van Beusechem and Valerio) In: Murray (1992) *Transgenesis: Applications of Gene Transfer*, John Wiley & Sons Ltd. Chichester, England, pp. 283–289.) To produce the rat or mouse model, a gene candidate which mimics a human disease is coupled to a strong promoter and injected into a fertilized egg, and the egg transferred into a pseudopregnant dam. The promoter may be activated at a specific time in a specific tissue type during fetal development or postnatally. Expression of the transgene is monitored by analysis of phenotype, tissue-specific mRNA expression, and challenged with experimental drug therapies. Examples of transgenes used as models of human disease include the investigation of the mutant amyloid precursor protein and apolipoprotein E genes in familial Alzheimer's Disease (Price and Sisodia (1998) Annu. Rev. Neurosci. 21:479–505).

Embryonic stem cells (ES) isolated from rodent embryos retain the potential to form an embryo. When ES cells are placed inside a carrier embryo, they resume normal development and contribute to all tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors for knockout strains contain a disease gene candidate modified to include a marker gene sequence which disrupts transcription and/or translation in vivo. The vector is introduced into ES cells by transformation methods such as electroporation, liposome delivery, microinjection, and the like which are well known in the art. The endogenous rodent gene is replaced by the disrupted disease gene through homologous recombination and integration during cell division. Then transformed ES cells are selected, identified, and preferably microinjected into mouse cell blastocysts such as those from the C57BL/6 mouse strain. The blastocysts are surgically transferred to pseudopregnant dams and the resulting chimeric progeny are genotyped and bred to produce heterozygous or homozygous strains.

ES cells are also used to study the differentiation of various cell types and tissues in vitro, such as neural cells, hematopoietic lineages, and cardiomyocytes (Bain et al. (1995) Dev. Biol. 168:342–357; Wiles and Keller (1991) Development 111:259–267; and Klug et al. (1996) J. Clin. Invest. 98:216–224). Recent developments demonstrate that ES cells derived from human blastocysts may also be manipulated in vitro to differentiate into eight separate cell lineages, including endoderm, mesoderm, and ectodermal cell types (Thomson(1998) Science 282:1145–1147).

As described herein, the uses of the nucleotide sequences, provided in the Sequence Listing of this application, are exemplary of known techniques and are not intended to reflect any limitation on their use in any technique that would be known to the person of average skill in the art. Furthermore, the nucleotide sequences provided in this application may be used in molecular biology techniques that have not yet been developed, provided the new techniques rely on properties of nucleotide sequences that are currently known to the person of ordinary skill in the art.

In gene knockout analysis, a region of a human disease gene candidate is enzymatically modified to include a non-mammalian gene such as the neomycin phosphotransferase gene (neo; Capecchi (1989) Science 244:1288–1292). The inserted coding sequence disrupts transcription and translation of the targeted gene and prevents biochemical synthesis of the disease candidate protein. The modified gene is transformed into cultured embryonic stem cells (described above), the transformed cells are injected into rodent blastulae, and the blastulae are implanted into pseudopregnant dams. Transgenic progeny are crossbred to obtain homozygous inbred lines.

Totipotent ES cells, present in the early stages of embryonic development, can be used to create knockin humanized animals (pigs) or transgenic animal models (mice or rats) of human diseases. With knockin technology, a region of a human gene is injected into animal ES cells, and the human sequence integrates into the animal cell genome by recombination. Totipotent ES cells which contain the integrated human gene are handled as described above. Inbred animals are studied and treated to obtain information on the analogous human condition. These methods have been used to model several human diseases. (See, e.g., Lee et al. (1998) Proc. Natl. Acad. Sci. 95:11371–11376; Baudoin et al. (1998) Genes Dev. 12:1202–1216; and Zhuang et al. (1998) Mol. Cell Biol. 18:3340–3349).

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus monkeys (*Macaca fascicularis, Macaca mulatta*) and common marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPs are the first choice test animal. In addition, NHPs and individual humans exhibit differential sensitivities to many drugs and toxins and can be classified as "extensive metabolizers" and "poor metabolizers" of these agents. For this reason, NHPs are the favored models for studying metabolism and toxicology of agents acted upon by the cytochrome $P_{450}$ family of enzymes.

In additional embodiments, the nucleotide sequences which encode the mammalian protein may be used in any molecular biology techniques that have yet to be developed, provided the new techniques rely on properties of nucleotide sequences that are currently known, including, but not limited to, such properties as the triplet genetic code and specific base pair interactions.

EXAMPLES

It is to be understood that this invention is not limited to the particular machines, materials and methods described. Although particular embodiments are described, equivalent embodiments may be used to practice the invention. The described embodiments are not intended to limit the scope of the invention which is limited only by the appended claims. The examples below are provided to illustrate the subject invention and are not included for the purpose of limiting the invention. For purposes of example, the preparation of the human corpus callosum cDNA library, CORPNOT02, is described.

I Representative cDNA Sequence Preparation

The human corpus callosum cDNA library CORPNOT02 was constructed from tissue obtained from a 74-year-old Caucasian male (specimen #RA95-09-0670; International Institute for the Advancement of Medicine, Exton Pa.) who died from Alzheimer's disease. The frozen tissue was homogenized and lysed in guanidinium isothiocyanate solution using a POLYTRON homogenizer (PT-3000; Brinkmann Instruments, Westbury N.J.). The lysate was centrifuged over a 5.7 M CsCl cushion using an SW28 rotor in an L8-70M ultracentrifuge (Beckman Coutten, Fullerton Calif.) for 18 hours at 25,000 rpm at ambient temperature. The RNA was extracted with acid phenol, pH 4.7, precipitated using 0.3 M sodium acetate and 2.5 volumes of ethanol, resuspended in RNAse-free water, and treated with DNase (Life Technologies) at 37° C. The RNA extraction and precipitation were repeated as before.

Messenger RNA (mRNA) was isolated using, the OLIGOTEX kit (Qiagen, Valencia Calif.) and used to construct the cDNA library. The mRNA was handled according to the recommended protocols in the SUPERSCRIPT plasmid system (Life Technologies) which contains a NotI primer-adaptor designed to prime the first strand cDNA synthesis at the poly(A) tail of mRNAs. Double stranded cDNA was blunted, ligated to EcoRI adaptors and digested with NotI (New England Biolabs, Beverly Mass.). The cDNAs were fractionated on a SEPHAROSE CL-4B column (Amersham Pharmacia Biotech), and those cDNAs exceeding 400 bp were ligated into the NotI and EcoRI sites of the pINCY 1 plasmid (Incyte Isemomics, Palo Alto Calif.). The plasmid was transformed into competent DH5α cells (Life Technologies) or ELECTROMAX DH10B cells (Life Technologies).

Plasmid DNA was released from the cells and purified using the REAL PREP 96 plasmid kit (Qiagen). The recommended protocol was employed except for the following changes: 1) the bacteria were cultured in 1 ml of sterile Terrific Broth (Life Technologies) with carbenicillin at 25 mg/l and glycerol at 0.4%; 2) after inoculation, the cultures were incubated for 19 hours and then lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were prepared using either a MICROLAB 2200 system (Hamilton) or a HYDRA microdispenser (Robbins Scientific, Sunnyvale Calif.) in combination with the DNA ENGINE thermal cyclers (MJ Research) and sequenced by the method of Sanger, F. and A. R. Coulson (1975; J. Mol. Biol. 94:441–448) using either an ABI PRISM 377 (Applied Biosystems) or MEGABACE (Amersham Pharmacia Biotech) sequencing system. Most of the isolates were sequenced according to standard ABI protocols and kits (Applied Biosystems). The solution volumes were used at 0.25×–1.0× concentrations. In the alternative, cDNAs were sequenced using solutions and dyes from Amersham Pharmacia Biotech.

II Identification, Extension, Assembly, and Analyses of the Sequences

Incyte clone 700145292 from ZOOSEQ database (Incyte Pharmaceuticals, Palo Alto Calif.) was used to identify Incyte Clone 5595953 from the LIFESEQ database (Incyte Pharmaceuticals). The first pass and extended cDNAs, SEQ ID NOs:3–11, which cluster with Incyte Clone 5595953 were assembled using Phred/Phrap or CONSED (Green, University of Washington) or the GCG Fragment assembly system (Genetics Computer Group, Madison Wis.). The assembled sequence was searched for open reading frames, and the coding region was translated using MACDNASIS PRO software (Hitachi Software Engineering). The full length nucleotide and amino acid sequences were analyzed by BLAST queries against databases such as the GenBank databases, SwissProt, BLOCKS, PRINTS, Prosite, and PFAM and by LASERGENE software (DNASTAR). Functional analyses of the amino acid sequences were performed using MOTIFS (Genetics Computer Group) and HMM algorithms. Antigenic index (Jameson-Wolf analysis) of the amino acid sequences were determined using LASERGENE software (DNASTAR). Then, the clones and assembled sequence were compared using BLAST across all mammalian libraries to identify homologous nucleic acid sequences, SEQ ID NOs:12–25.

III Sequence Similarity

Sequence similarity was calculated as percent identity based on comparisons between at least two nucleic acid or amino acid sequences using the clustal method of the MEGALIGN program (DNASTAR). The clustal method uses an algorithm which groups sequences into clusters by examining the distances between all pairs. After the clusters are aligned pairwise, they are realigned in groups. Percent similarity between two sequences, sequence A and sequence B, is calculated by dividing the length of sequence A, minus the number of gap residues in sequence A, minus the number of gap residues in sequence B, into the sum of the residue matches between sequence A and sequence B, times one hundred. Gaps of very low or zero similarity between the two sequences are not included.

IV Northern Analysis

Northern analysis is a laboratory technique used to detect the presence of a transcript of a gene and involves the hybridization of a labeled nucleotide sequence to a membrane on which RNAs from a particular cell type or tissue have been bound.

Analogous computer techniques applying BLAST were used to search for identical or related molecules in nucleotide databases such as GenBank or LIFESEQ (Incyte Isemomics). Sequence-based analysis is much faster than membrane-based hybridization, and the sensitivity of the computer search can be modified to determine whether any particular match is categorized as exact or similar. The basis of the search is the product score which is defined as: (percent sequence identity x percent maximum BLAST score) divided by 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

The results of northern analyses are reported as a percentage distribution of libraries in which the transcript encoding the mammalian protein occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease categories included cancer, inflammation/trauma, cell proliferation, and neurological. For each category, the number of libraries expressing the sequence was counted and divided by the total number of libraries across all categories.

V Extension of Polynucleotides

The nucleic acid sequence of SEQ ID NO:1 was produced by extension of Incyte cDNA clones using oligonucleotide primers. One primer was synthesized to initiate 5' extension of the known fragment, and the other, to initiate 3' extension of the known fragment. The initial primers were designed using OLIGO software (Molecular Biology Insights) to be about 22 to 30 nucleotides in length, to have a GC content of about 50%, and to anneal to the target sequence at temperatures of about 68° C. to about 72° C. Any fragment which would result in hairpin structures and primer-primer dimerizations was avoided. Selected human cDNA libraries were used to extend the sequence. If more than one extension is needed, additional or nested sets of primers are designed.

High fidelity amplification was obtained by performing PCR in 96-well plates using the PTC-200 (MJ Research). The reaction mix contained DNA template, 200 nmol of each primer, reaction buffer containing $Mg^{2+}$, $(NH_4)_2SO_4$, and β-mercaptoethanol TAQ DNA polymerase (Amersham Pharmacia Biotech), ELONGASE enzyme (Life Technologies), and Pfu DNA polymerase (Stratagene), with the following parameters for primer pair selected from the plasmid: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, parameters for the primer pair, T7 and SK+ (Stratagene), were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 µl PICOGREEN quantitation reagent (0.25% (v/v); Molecular Probes) dissolved in 1×TE and 0.5 µl of undiluted PCR product into each well of an opaque fluorimeter plate (Corning Life Sciences Acton, Mass.) and allowing the DNA to bind to the reagent. The plate was scanned in a Fluoroskan II (Labsystems Oy, Helsinki, Finland) to measure the fluorescence of the sample and to quantify the concentration of DNA. A 5 µl to 10 µl aliquot of the reaction mixture was analyzed by electrophoresis on a 1% agarose mini-gel to determine which reactions were successful in producing longer sequence.

The extended sequences were desalted, concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested fragments were separated on about 0.6–0.8% agarose gels, fragments were excised as visualized under UV light, and agar removed/digested with AGARACE (Promega). Extended fragments were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transformed into competent *E. coli* cells. Transformed cells were selected on antibiotic-containing media, and individual colonies were picked and cultjred overnight at 37° C. in 384-well plates in LB/2× carbenicillin liquid media.

The cells were lysed, and DNA was amplified using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the conditions described above. Samples were diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Applied Biosystems).

In like manner, the nucleotide sequence of SEQ ID NO:1 is used to obtain regulatory sequences using the procedure above, oligonucleotides designed for outward extension, and a genomic library.

VI Labeling of Probes and Hybridization Analyses

Polynucleotide sequences are isolated from a biological source and applied to a substrate for standard nucleic acid hybridization protocols by one of the following methods. A mixture of target nucleic acids, a restriction digest of genomic DNA, is fractionated by electrophoresis through an 0.7% agarose gel in 1× TAE [Tris-acetate-ethylenediamine tetraacetic acid (EDTA)] running buffer and transferred to a nylon membrane by capillary transfer using 20×saline sodium citrate (SSC). Alternatively, the target nucleic acids are individually ligated to a vector and inserted into bacterial host cells to form a library. Target nucleic acids are arranged on a substrate by one of the following methods. In the first method, bacterial cells containing individual clones are robotically picked and arranged on a nylon membrane. The membrane is placed on bacterial growth medium, LB agar containing carbenicillin, and incubated at 37° C. for 16 hours. Bacterial colonies are denatured, neutralized, and digested with proteinase K. Nylon membranes are exposed to UV irradiation in a STRATALINKER UV-crosslinker (Stratagene) to cross-link DNA to the membrane.

In the second method, target nucleic acids are amplified from bacterial vectors by thirty cycles of PCR using primers complementary to vector sequences flanking the insert. Amplified target nucleic acids are purified using SEPHACRYL-400 resin (Amersham Pharmacia Biotech). Purified target nucleic acids are robotically arrayed onto a glass microscope slide (Corning Science Products, Corning N.Y.). The slide was previously coated with 0.05% aminopropyl silane (Sigma-Aldrich, St. Louis Mo.) and cured at 110° C. The arrayed glass slide (microarray) is exposed to UV irradiation in a STRATALINKER UV-crosslinker (Stratagene).

cDNA probe sequences are made from mRNA templates. Five micrograms of mRNA is mixed with 1 μg random primer (Life Technologies), incubated at 70° C. for 10 minutes, and lyophilized. The lyophilized sample is resuspended in 50 μl of 1×first strand buffer (cDNA Synthesis systems; Life Technologies) containing a dNTP mix, [α-$^{32}$P] dCTP, dithiothreitol, and MMLV reverse transcriptase (Stratagene), and incubated at 42° C. for 1–2 hours. After incubation, the probe is diluted with 42 μl dH$_2$O, heated to 95° C. for 3 minutes, and cooled on ice. mRNA in the probe is removed by alkaline degradation. The probe is neutralized, and degraded mRNA and unincorporated nucleotides are removed using a PROBEQUANT G-50 Micro-Column (Amersham Pharmacia Biotech). Probes can be labeled with fluorescent nucleotides, Cy3-dCTP or Cy5-dCTP (Amersham Pharmacia Biotech), in place of the radiolabeled nucleotide, [$^{32}$P]dCTP.

Hybridization is carried out at 65° C. in a hybridization buffer containing 0.5 M sodium phosphate (pH 7.2), 7% SDS, and 1 mM EDTA. After the substrate is incubated in hybridization buffer at 65° C. for at least 2 hours, the buffer is replaced with 10 ml of fresh buffer containing the probe sequences. After incubation at 65° C. for 18 hours, the hybridization buffer is removed, and the substrate is washed sequentially under increasingly stringent conditions, up to 40 mM sodium phosphate, 1% SDS, 1 mM EDTA at 65° C. To detect signal produced by a radiolabeled probe hybridized on a membrane, the substrate is exposed to a PHOSPHORIMAGER cassette (Amersham Pharmacia Biotech), and the image is analyzed using IMAGEQUANT data analysis software (Amersham Pharmacia Biotech). To detect signals produced by a fluorescent probe hybridized on a microarray, the substrate is examined by confocal laser microscopy, and images are collected and analyzed using GEMTOOLS gene expression analysis software (Incyte Pharmaceuticals).

VII Complementary Polynucleotides

Sequences complementary to the polynucleotide, or a fragment thereof, are used to detect, decrease, or inhibit gene expression. Although use of oligonucleotides comprising from about 15 to about 30 base pairs is described, essentially the same procedure is used with with larger or smaller fragments or their derivatives (PNAs). Oligonucleotides are designed using OLIGO software (Molecular Biology Insights) and SEQ ID NO:1 or its fragments, SEQ ID NO:3–9. To inhibit transcription by preventing promoter binding, a complementary oligonucleotide is designed to bind to the most unique 5' sequence, most preferably about 10 nucleotides before the initiation codon of the open reading frame. To inhibit translation, a complementary oligonucleotide is designed to prevent ribosomal binding to the mRNA encoding the mammalian protein.

VIII Expression of the Mammalian Protein

Expression and purification of the mammalian protein are achieved using bacterial or virus-based expression systems. For expression in bacteria, cDNA is subcloned into a vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into bacterial hosts, e.g., BL21(DE3). Antibiotic resistant bacteria express the mammalian protein upon induction with isopropyl beta-D-thiogalactopyranoside (IPTG). Expression in eukaryotic cells is achieved by infecting *Spodoptera frugiperda* (Sf9) insect cells with recombinant baculovirus, *Autographica californica* nuclear polyhedrosis virus. The nonessential polyhedrin gene of baculovirus is replaced with the mammalian cDNA by either homologous recombination or bacterial-mediated transposition involving transfer plasmid intermediates. Viral infectivity is maintained and the strong polyhedrin promoter drives high levels of cDNA transcription.

In most expression systems, the mammalian protein is synthesized as a fusion protein with, e.g., glutathione S-transferase (GST) or a peptide epitope tag, such as FLAG, permitting rapid, single-step, affinity-based purification of recombinant fusion protein from crude cell lysates. GST enables the purification of fusion proteins on immobilized glutathione under conditions that maintain protein activity and antigenicity (Amersham Pharmacia Biotech). Following purification, the GST moiety can be proteolytically cleaved from the mammalian protein at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (supra, unit 16). Purified mammalian protein obtained by these methods can be used directly in the following activity assay.

IX Functional Assays

Protein function is assessed by expressing the sequences encoding LMTF at physiologically elevated levels in mammalian cell culture. The polynucleotide is subcloned into pCMV SPORT vector (Life Technologies), which contains the strong cytomegalovirus promoter, and 5–10 μg of the vector is transformed into a endothelial or hematopoietic human cell line using electroporation. An additional 1–2 μg of a plasmid containing sequence encoding CD64-GFP (Clontech) is co-transformed to provide an fluorescent marker to identify transformed cells using flow cytometry (FCM).

The influence of the introduced genes on expression can be assessed using purified populations of these transformed cells. Since CD64-GFP, which is expressed on the surface of transformed cells, binds to conserved regions of human immunoglobulin G (IgG), the transformed cells is separated using magnetic beads coated with either huinan IgG or antibody against CD64 (DYNAL, Lake Success N.Y.). mRNA is purified from the cells and analyzed by hybridization techniques.

X Production of LMTF Specific Antibodies

LMTF substantially purified using polyacrylamide gel electrophoresis is used to immunize rabbits and to produce antibodies using standard protocols.

Alternatively, the amino acid sequence of LMTF is analyzed using LASERGENE software (DNASTAR) to determine regions of high immunogenicity. An immunogenic epitope such as those near the C-terminus or in hydrophilic regions is selected, synthesized, and used to raise antibodies by means known to those of skill in the art.

Typically, epitopes of about 15 residues in length are produced using an ABI 431A Peptide synthesizer (Applied Biosystems) using Fmoc-chemistry and coupled to KLH (Sigma-Aldrich) by reaction with N-maleimidobenzoyl-N-hydroxysuccinimide ester to increase immunogenicity. Rabbits are immunized with the epitope-KLH complex in complete Freund's adjuvant. Immunizations are repeated at intervals thereafter in incomplete Freund's adjuvant. After a sufficient period of time, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

XI Purification of Naturally Occurring Protein Using Specific Antibodies

Naturally occurring or recombinant mammalian protein is substantially purified by immunoaffinity chromatography using antibodies specific for the protein. An immunoaffinity column is constructed by covalently coupling the antibody to CNBr-activated SEPHAROSE resin (Amersham Pharmacia Biotech). Media containing the protein is passed over the immunoaffinity column, and the column is washed using high ionic strength buffers in the presence of detergent to allow preferential absorbance of the protein. After coupling, the column is eluted using a buffer of pH 2–3 or a high concentration of urea or thiocyanate ion to disrupt antibody/protein binding, and the protein is collected.

XII Screening Molecules for Specific Binding with the Polynucleotide or Protein

The nucleic acid sequence, or fragments thereof, or the protein, or portions thereof, are labeled with $^{32}$P-dCTP, Cy3-dCTP, Cy5-dCTP (Amersham Pharmacia Biotech), or BIODIPY or FITC (Molecular Probes, Eugene Oreg.), respectively. Libraries of candidate molecules previously arranged on a substrate are incubated in the presence of labeled nucleic acid sequence or protein. After incubation, the substrate is washed, and any position on the substrate retaining label, which indicates specific binding or complex formation, is assayed, and the binding molecule is identified. Data obtained using different concentrations of the nucleic acid or protein are used to calculate affinity between the labeled nucleic acid or protein and the bound molecule.

XIII Demonstration of Protein Activity

LMTF activity is measured by its ability to modulate transcription of a reporter gene. The assay entails the use of a reporter gene construct that consists of a transcription factor response element fused upstream to sequences encoding the $E.\ coli$ β-galactosidase enzyme (LacZ). Sequences encoding LMTF are subcloned into a mammalian expression vector containing a strong promoter that drives high levels of cDNA expression. Vectors of choice include PCMV SPORT (Life Technologies) and PCR 3.1 (Invitrogen, Carlsbad Calif.), both of which contain the cytomegalovirus promoter. The recombinant vector and reporter gene construct are co-transfected into a human cell line, preferably of neuronal origin, using either liposome formulations or electroporation. The amount of β-galactosidase enzyme activity associated with LMTF transfected cells, relative to control cells transfected with the reporter construct alone, is proportional to the amount of transcription modulated by the LMTF gene product.

TABLE 1

| Nucleic Acid SEQ ID NO: | Incyte Clone Number | Nucleotide Length | Source | Library | Coverage | Percent Identity |
|---|---|---|---|---|---|---|
| 3 | 1479946F6 | 502 | Homo sapiens | CORPNOT02 | 1–502 | n/a |
| 4 | 3241390F6 | 529 | Homo sapiens | COLAUCT01 | 281–801 | n/a |
| 5 | 1432520R1 | 562 | Homo sapiens | BEPINON01 | 599–1178 | n/a |
| 6 | 4534217H1 | 254 | Homo sapiens | OVARNOT12 | 1152–1414 | n/a |
| 7 | 2191992H1 | 238 | Homo sapiens | THYRTUT03 | 1200–1437 | n/a |
| 8 | 1320132T1 | 661 | Homo sapiens | BLADNOT04 | 1299–1957 | n/a |
| 9 | 1516707T1 | 624 | Homo sapiens | PANCTUT01 | 1445–2070 | n/a |
| 10 | 5595953H1 | 252 | Homo sapiens | COLCDIT03 | 1592–1845 | n/a |
| 11 | 1988906R6 | 302 | Homo sapiens | LUNGAST01 | 1851–2092 | n/a |
| 12 | 700712962H1 | 144 | Macaca fascicularis | MNBFNOT02 | 12–156 | 92.4 |
| 13 | 700715135H1 | 274 | Macaca fascicularis | MNBCNOT01 | 292–564 | 93.1 |
| 14 | 701253541H1 | 273 | Mus musculus | MOLUDIT07 | 560–1032 | 71.2 |
| 15 | 701252210H1 | 250 | Mus musculus | MOLUDIT07 | 1564–1831 | 81.0 |
| 16 | 700545683H1 | 272 | Rattus norvegicus | RASPNOT01 | 1–271 | 52.2 |
| 17 | 700145292H1 | 257 | Rattus norvegicus | RAPRNOT01 | 191–488 | 44.7 |
| 18 | 700861443H1 | 239 | Rattus norvegicus | RABGNOT02 | 338–591 | 63.2 |
| 19 | 700225363H1 | 302 | Rattus norvegicus | RAKINOT01 | 479–780 | 86.4 |
| 20 | 700643425H1 | 286 | Rattus norvegicus | RABUNOT01 | 593–879 | 81.1 |
| 21 | 700525920H1 | 285 | Rattus norvegicus | RABMNOT01 | 783–1066 | 77.2 |
| 22 | 700773927H1 | 270 | Rattus norvegicus | RABONOT01 | 1001–1197 | 54.8 |
| 23 | 700513679H1 | 283 | Rattus norvegicus | RASNNOT01 | 1318–1594 | 72.1 |
| 24 | 700767486H1 | 266 | Rattus norvegicus | RAHYNOT01 | 1594–1876 | 73.7 |
| 25 | 700327166H1 | 199 | Rattus norvegicus | RASNNOT01 | 1813–2008 | 74.4 |

What is claimed is:

1. A substantially purified maimnalian nucleic acid sequence encoding the amino acid sequence of SEQ ID NO:2.

2. An isolated and purified mammalian nucleic acid sequence selected from SEQ ID NO:1 or SEQ ID NO:3–25.

3. A nucleic acid sequence selected from SEQ ID NO:1 or 3–25 on a microarray.

4. The complement of the nucleic acid sequence of claim 1.

5. The complement of the nucleic acid sequence of claim 2.

6. An expression vector comprising the nucleic acid sequence of claim 1.

7. A host cell containing the expression vector of claim 6.

8. A method for producing a protein, the method comprising the steps of:

(a) culturing the host cell of claim 7 under conditions for expression of the protein; and (b) recovering the protein from the host cell culture.

9. A probe selected from the mammalian nucleic acid sequences of claim 2.

10. A method for detecting a mammalian nucleic acid sequence in a sample, the method comprising the steps of:

(a) hybridizing the probe of claim 6 to at least one nucleic acid sequence in the sample, thereby forming a hybridization complex; and (b) detecting the hybridization complex, wherein the presence of the hybridization complex correlates with the presence of the mammalian nucleic acid sequence in the sample.

11. The method of claim 10 further comprising amplifying the nucleic acid sequences of the sample prior to hybridization.

12. A method of using a mammalian nucleic acid sequence to screen a library of molecules to identify at least one molecule which specifically binds the nucleic acid, the method comprising:

(a) providing a library of molecules;

(b) combining the nucleic acid sequence of claim 1 with a library of molecules under conditions to allow specific binding; and (c) detecting specific binding, thereby identifying a molecule which specifically binds the nucleic acid sequence.

13. The library of claim 12 wherein the library is selected from DNA molecules, RNA molecules, peptide nucleic acids, peptides, and proteins.

* * * * *

SEQUENCE LISTING

<160> NUMBER OF SEQ ID NOS: 27

<210> SEQ ID NO 1
<211> LENGTH: 2092
<212> TYPE: DNA
<213> ORGANISM: Homo sapiens
<220> FEATURE:
<221> NAME/KEY:
<223> OTHER INFORMATION: 5595953
<300> PUBLICATION INFORMATION:

<400> SEQUENCE: 1

```
gggcctttta tctcggtgct gccgggggag gcgggaggag gagacaccag gggtggccct      60
gagcgccggc gacacctttc ctggactata aattgagcac ctgggatggg taggggggcca    120
acgcagtcac cgccgtccgc agtcacagtc cagccactga ccgcagcagc gcccttgcgt    180
acagccgctt gcagcgagaa cactgaattg ccaacgagca ggagagtctc aaggcgcaag    240
aggaggccag ggctcgaccc acagagcacc ctcagccatc gcgagtttcc gggcgccaaa    300
gccaggagaa gccgcccatc ccgcagggcc ggtctgccag cgagacgaga gttggcgagg    360
gcggaggagt gccgggaatc ccgccacacc ggctatagcc aggcccccag cgcgggcctt    420
ggagagcgcg tgaaggcggg catccccttg acccggccga ccatcccgt gcccctgcgt     480
ccctgcgctc caacgtccgc gcggccacca tgatgcaaat ctgcgacacc tacaaccaga    540
agcactcgct ctttaacgcc atgaatcgct tcattggcgc cgtgaacaac atggaccaga    600
cggtgatggt gccagcttg ctgcgcgacg tgcccctggc tgaccccggg ttagacaacg     660
atgttggcgt ggaggtaggc ggcagtggcg gctgcctgga ggagcgcacg ccccccagtcc    720
ccgactcggg aagcgccaat ggcagctttt tcgcgccctc tcgggacatg tacagccact    780
acgtgcttct caagtccatc cgcaacgaca tcgagtgggg ggtcctgcac cagccgcctc    840
caccggctgg gagcgaggag ggcagtgcct ggaagtccaa ggacatcctg gtggacctgg    900
gccacttgga gggtgcggac gccggcgaag aagacctgga acagcagttc cactaccacc    960
tgcgcgggct gcacactgtg ctctcgaaac tcacgcgcaa agccaacatc ctcactaaca   1020
gatacaagca ggagatcggc ttcggcaatt ggggccactg aggcgtggcg cccgtggctg   1080
cccagcacct tcttcgaccc atctcaccct ctctcattcc tcaaagcttt ttttttttt   1140
cctggctggg gggcgggaag ggcagactgc aaactggggg gctgcgtacg tgcaggaggc   1200
gcggtggggc tgcgtggagg aggggccac gtgtgagaga aagaaaatg gtggccggag     1260
atgggagggc ccaaggaacc tcctgggagg gggcctgcat tctatgttgg tgggaatggg   1320
actgggctga cgccctgcat tcagcctgtg cctttcctgg ggtttctttt ctgttctttt   1380
cggaggagag ggcccgagaa ggggccatac cagggcgcgg cgctggggttg ccacacttgg   1440
gaaagcagcc cggagctggg tgctggggaa ggcggggcgc gtagcctccc gccgccctgc   1500
ggttgggccg gtggaggccc aggcgttgct aggattgcat cagttttcct gtttgcacta   1560
tttcttttg taacattggc cctgtgtgaa gtatttcgaa tctcctcctt gctctgaaac     1620
ttcagcgatt ccattgtgat aagcgcacaa acagcactgt ctgtcggtaa tcggtactac   1680
tttattaatg atttttctgtt acactgtata gtagtcctat ggcaccccca ccccatccct   1740
ttcgtgccac tcccgtcccc accccaccc cagtgtgtat aagctggcat ttcgccagct   1800
tgtacgtagc ttgccactca gtgaaaataa taacattatt atgagaaagt ggacttaacc   1860
gaaatggaac caactgacat tctatcgtgt tgtacataga atgatgaagg gttccactgt   1920
```

-continued

```
tgttgtatgt cttaaattta tttaaaactt tttttaatcc agatgtagac tatattctaa    1980
aaaataaaaa agcaaatgtg tcaactaaat tggacaagcg tctggtcctc attaatctgc    2040
caatgaatgg tttcgtcatt aaataaaaat caatttaatt gatttactag ca            2092
```

<210> SEQ ID NO 2  
<211> LENGTH: 183  
<212> TYPE: PRT  
<213> ORGANISM: Homo sapiens  
<220> FEATURE:  
<221> NAME/KEY:  
<223> OTHER INFORMATION: 5595953  
<300> PUBLICATION INFORMATION:

<400> SEQUENCE: 2

```
Met Met Gln Ile Cys Asp Thr Tyr Asn Gln Lys His Ser Leu Phe
 1               5                  10                  15

Asn Ala Met Asn Arg Phe Ile Gly Ala Val Asn Asn Met Asp Gln
                20                  25                  30

Thr Val Met Val Pro Ser Leu Leu Arg Asp Val Pro Leu Ala Asp
                35                  40                  45

Pro Gly Leu Asp Asn Asp Val Gly Val Glu Val Gly Gly Ser Gly
                50                  55                  60

Gly Cys Leu Glu Glu Arg Thr Pro Pro Val Pro Asp Ser Gly Ser
65                  70                  75

Ala Asn Gly Ser Phe Phe Ala Pro Ser Arg Asp Met Tyr Ser His
                80                  85                  90

Tyr Val Leu Leu Lys Ser Ile Arg Asn Asp Ile Glu Trp Gly Val
                95                 100                 105

Leu His Gln Pro Pro Pro Ala Gly Ser Glu Glu Gly Ser Ala
               110                 115                 120

Trp Lys Ser Lys Asp Ile Leu Val Asp Leu Gly His Leu Glu Gly
               125                 130                 135

Ala Asp Ala Gly Glu Glu Asp Leu Glu Gln Gln Phe His Tyr His
               140                 145                 150

Leu Arg Gly Leu His Thr Val Leu Ser Lys Leu Thr Arg Lys Ala
               155                 160                 165

Asn Ile Leu Thr Asn Arg Tyr Lys Gln Glu Ile Gly Phe Gly Asn
               170                 175                 180

Trp Gly His
```

<210> SEQ ID NO 3  
<211> LENGTH: 502  
<212> TYPE: DNA  
<213> ORGANISM: Homo sapiens  
<220> FEATURE:  
<221> NAME/KEY: unsure  
<222> LOCATION: 181, 317, 363, 393, 402, 421, 432, 458, 461, 463, 470  
<221> NAME/KEY: unsure  
<222> LOCATION: 478, 482, 494  
<223> OTHER INFORMATION: a or g or c or t, unknown, or other  
<220> FEATURE:  
<221> NAME/KEY:  
<223> OTHER INFORMATION: 1479946F6  
<300> PUBLICATION INFORMATION:

<400> SEQUENCE: 3

```
gggccttttta tctcggtgct gccgggggag gcgggaggag agacaccag gggtggccct     60 gagcgccggc gacacctttc ctggactata aattgagcac ctgggatggg taggggggcca   120
```

| | |
|---|---|
| acgcatcacc gccgtccgca gtcacagtcc agccactgac cgcagcagcg cccttgcgta | 180 |
| nagccgcttg cagcgagaac actgaattgc caacgagcag gagagtctca aggcgcaaga | 240 |
| ggaggccagg ggctcgaccc acagagcacc ctcagccatc gcgagtttcc gggcgccaaa | 300 |
| gccaggagaa gccgccnatc ccgcaaggcc cggtctgcca gcgagacgag attggcgagg | 360 |
| gcngaagagt gccgggaatc ccgccacacc ggntatagca anccccagc gcgggctttg | 420 |
| naaacgcctg angcgggcat cccttgaccg gcgacatncc ntncctgcn tcctggntc | 480 |
| ancttcgggc gcancatatt ac | 502 |

<210> SEQ ID NO 4
<211> LENGTH: 529
<212> TYPE: DNA
<213> ORGANISM: Homo sapiens
<220> FEATURE:
<221> NAME/KEY: unsure
<222> LOCATION: 48, 172, 214, 348, 364, 414, 417, 428, 430, 436
<221> NAME/KEY: unsure
<222> LOCATION: 471, 491, 495, 503, 511, 523
<223> OTHER INFORMATION: a or g or c or t, unknown, or other
<220> FEATURE:
<221> NAME/KEY:
<223> OTHER INFORMATION: 3241390F6
<300> PUBLICATION INFORMATION:

<400> SEQUENCE: 4

| | |
|---|---|
| gcgagtttcc gggcgccaaa gccaggagaa gccgcccatc ccgcaggnca ggtctgccag | 60 |
| cgagacgaga gttggcgagg gcggaggagt gccgggaatc ccgccacacc ggctatagcc | 120 |
| aggcccccag cgcgggcctt ggagagcgcg tgaaggcggg catcccttg anccggccga | 180 |
| ccatccccgt gccctgcgt ccctgcgctc caangtccgc gcggccacca tgatgcaaat | 240 |
| ctgcgacacc tacaaccaga agcactcgct ctttaacgcc atgaatcgct tcattggcgc | 300 |
| cgtgaacaac atggaccaga cggtgatggt gcccagcttg tgcgcgangt gccctggct | 360 |
| gacnccgggt tagacaacga tgttggcgtg gaggtaagcg gcaatggcgg cttnctngag | 420 |
| gagcgcangn ccccanttcc cgactcggga agcgccaatg gagctttttt ngggcctct | 480 |
| tggggacaat nttanaagcc aantaagtgg nttctcaaag ttncatccg | 529 |

<210> SEQ ID NO 5
<211> LENGTH: 562
<212> TYPE: DNA
<213> ORGANISM: Homo sapiens
<220> FEATURE:
<221> NAME/KEY: unsure
<222> LOCATION: 288, 289, 291, 293, 313, 434, 514, 560
<223> OTHER INFORMATION: a or g or c or t, unknown, or other
<220> FEATURE:
<221> NAME/KEY:
<223> OTHER INFORMATION: 1432520R1
<300> PUBLICATION INFORMATION:

<400> SEQUENCE: 5

| | |
|---|---|
| gacggtgatg gtgcccagct tgctgcgcga cgtgccctg gctgacccg ggttagacaa | 60 |
| cgatgttggc gtggaggtag gcggcagtgg cggctgcctg gaggagcgca cgcccccagt | 120 |
| ccccgactcg ggaagcgcca atggcagctt tttcgcgccc tctcgggaca tgtacagcca | 180 |
| ctacgtgctt ctcaagtcca tccgcaacga catcgagtgg ggggtcctgc accagccgcc | 240 |
| tccaccggct gggagcgagg agggcagtgc ctggaagtcc aaggacannc ngntggacct | 300 |
| gggccacttg ganggtgcgg acgccggcga agaagacctg gaacagcagt tccactacca | 360 |
| cctgcgcggg ctgcacactg tgtctcgaaa ctcacgcgca aagccaacat cctcactaac | 420 |

```
agtacaagca ggantcggtt cggaattggg ggcactgagg cgtggcgccc gtggctgccc      480 agaactttc gaccatctaa cctctctatt cctnaagctt ttttttttc cggctggggg       540 cggaaggcaa ctgcaaattn gg                                              562
```

<210> SEQ ID NO 6
<211> LENGTH: 254
<212> TYPE: DNA
<213> ORGANISM: Homo sapiens
<220> FEATURE:
<221> NAME/KEY: unsure
<222> LOCATION: 80, 215, 238, 239, 242, 243, 244, 249
<223> OTHER INFORMATION: a or g or c or t, unknown, or other
<220> FEATURE:
<221> NAME/KEY:
<223> OTHER INFORMATION: 4534217H1
<300> PUBLICATION INFORMATION:

<400> SEQUENCE: 6

```
gggcagactg caaactgggg ggctgcgtac gtgcaggagg cgcggtgggg ctgcgtggag      60
gagggggcca cgtgtgagan agaagaaaat ggtggccgga gatgggaggg cccaaggaac     120
ctcctgggag ggggcctgca ttctatgttg gtgggaatgg gactgggctg acgccctgca    180
ttcagcctgt gcctttcctg gggtttcttt tctgntcttt tcggaggaga aggcccgnna    240
annngccana ccaa                                                      254
```

<210> SEQ ID NO 7
<211> LENGTH: 238
<212> TYPE: DNA
<213> ORGANISM: Homo sapiens
<220> FEATURE:
<221> NAME/KEY: unsure
<222> LOCATION: 19, 133
<223> OTHER INFORMATION: a or g or c or t, unknown, or other
<220> FEATURE:
<221> NAME/KEY:
<223> OTHER INFORMATION: 2191992H1
<300> PUBLICATION INFORMATION:

<400> SEQUENCE: 7

```
cgcggtgggg ctgcgtggng gagggggcca cgtgtgagag agaagaaaat ggtggccgga      60
gatgggaggg cccaaggaac ctcctgggag ggggcctgca ttctatgttg gtgggaatgg    120
gactgggctg acnccctgca ttcagcctgt gcctttcctg gggtttcttt tctgttcttt    180
tcggaggaga gggcccgaga aggggccata ccagggcgcg cgctgggtt gccacact       238
```

<210> SEQ ID NO 8
<211> LENGTH: 661
<212> TYPE: DNA
<213> ORGANISM: Homo sapiens
<220> FEATURE:
<221> NAME/KEY: unsure
<222> LOCATION: 2, 5, 65, 68, 70, 75, 96, 104, 107, 110, 116, 131
<221> NAME/KEY: unsure
<222> LOCATION: 194, 195, 198, 199, 200, 204, 225, 227, 235, 309
<221> NAME/KEY: unsure
<222> LOCATION: 469, 534, 536, 559, 563, 591, 603, 604, 612, 619
<221> NAME/KEY: unsure
<222> LOCATION: 632, 657
<223> OTHER INFORMATION: a or g or c or t, unknown, or other
<220> FEATURE:
<221> NAME/KEY:
<223> OTHER INFORMATION: 1320132T1
<300> PUBLICATION INFORMATION:

<400> SEQUENCE: 8

```
tnganttaaa aaaagttttta aataaattta agacatacca acaacagtgg aaaccttcat      60
cattntangn acaanacgat agaatgtcag ttgggnccat ttcngtnaan tccacnttct     120
cataataatg ntattatttt cactgagtgg caagctacgt acaagctggc gaaatgccag     180
cttatacaca ctgnngtnnn ggtngggacg ggagtggcac gaaangnatg gggtngggt      240 gccataggac tactatacag tgtaacagaa atcattaat aaagtagtac cgattaccga      300
cagacagtnc tgtttgtgcg cttatcacaa tggaatcgct gaagtttcag agcaaggagg    360
agattcgaaa tacttcacac agggccaatg ttacaaaaag aaatagtgca acaggaaaa     420 ctgatgcaat cctagcaacg cctgggcctc caccggccca accgcaggnt gcgggaggct    480
acgcgccccg ccttcccag cacccagctc cgggctgctt tcccaagtgt tgcnanccaa     540
cgccgcgccc tggtattgnc ccntctcggg cctttcctcc gaaagaacc ngaaagaacc     600 ccnngaaagg cncaggctna attcagggcg tnacccagtt ccattcccac caacttngat    660
t                                                                     661

<210> SEQ ID NO 9
<211> LENGTH: 624
<212> TYPE: DNA
<213> ORGANISM: Homo sapiens
<220> FEATURE:
<221> NAME/KEY: unsure
<222> LOCATION: (302)...(307), 330, 331, 334, 560, 572, 574, 577
<221> NAME/KEY: unsure
<222> LOCATION: 593, 609
<223> OTHER INFORMATION: a or g or c or t, unknown, or other
<220> FEATURE:
<221> NAME/KEY:
<223> OTHER INFORMATION: 1516707T1
<300> PUBLICATION INFORMATION:

<400> SEQUENCE: 9 attttattt aatgacgaaa ccattcattg gcagattaat gaggaccaga cgcttttcca      60
atttagttga cacatttgct ttttattttt ttagaatata gtctacatct ggattaaaaa    120
aagttttaaa taaatttaag acatacaaca acagtggaac ccttcatcat tctatgtaca    180
acacgataga atgtcagttg gttccatttc ggttaagtcc actttctcat aataatgtta   240
ttattttcac tgagtggcaa gctacgtaca agctggcgaa atgccagctt atacacactg   300
gnnnnnnggt ggggacggga gtggcacgan angnatgggg tggggtgcc ataggactac    360 tatacagtgt aacagaaaat cattaataaa gtagtaccga ttaccgacag acagtgctgt   420
ttgtgcgctt atcacaatgg aatcgctgaa gtttcagagc aaggaggaga ttcgaaatac   480
ttcacacagg gccaatgtta caaaagaaa tagtgcaaac aggaaaactg atgcaatcct   540
agcaacgcct gggcctccan cggcccaacc gnangcngcg ggaggctacg cgnccgctt    600 ccccagcanc cagctccggg gtgt                                          624

<210> SEQ ID NO 10
<211> LENGTH: 252
<212> TYPE: DNA
<213> ORGANISM: Homo sapiens
<220> FEATURE:
<221> NAME/KEY: unsure
<222> LOCATION: 186, 189, 195, 196, 200, 204, 208, 213, 222, 226
<221> NAME/KEY: unsure
<222> LOCATION: 228, 236, 244, 248, 251
<223> OTHER INFORMATION: a or g or c or t, unknown, or other
<220> FEATURE:
<221> NAME/KEY:
<223> OTHER INFORMATION: 5595953H1
<300> PUBLICATION INFORMATION:
```

<400> SEQUENCE: 10

```
atttcgaatc tcctccttgc tctgaaactt cagcgattcc attgtgataa gcgcacaaac      60
agcactgtct gtcggtaatc ggtactactt tattaatgat tttctgttac actgtatagt     120
agtcctatgg caccccccacc ccatcccttt cgtgccactc ccgtcccac ccccacccca     180
gggggntang cgggnntttn gccngctnga cgnagctggc cnctcngnga aaatantacc     240
tttnttgngg ng                                                         252
```

<210> SEQ ID NO 11
<211> LENGTH: 302
<212> TYPE: DNA
<213> ORGANISM: Homo sapiens
<220> FEATURE:
<221> NAME/KEY: unsure
<222> LOCATION: 89, 186, 251, 252, 254, 255, 258, 259, 260, 267, 268
<221> NAME/KEY: unsure
<222> LOCATION: 278, 281, 283, 286, 291, 292, 294, 297
<223> OTHER INFORMATION: a or g or c or t, unknown, or other
<220> FEATURE:
<221> NAME/KEY:
<223> OTHER INFORMATION: 1988906R6
<300> PUBLICATION INFORMATION:

<400> SEQUENCE: 11

```
ggacttaacc gaaatggaac caactgacat tctatcgtgt tgtacataga atgatgaagg      60
gttccactgt tgttgtatgt cttaaattna ttttaaactt tttttaatcc agatgtagac     120
tatattctaa aaataaaaa agcaaatgtg tcaactaaat tggacaagcg tctggtcctc     180
attaanctgc caatgaatgg tttcgtcatt aaataaaat caatttaatt gatttactag     240
caaaagtaga nnannaannn aaaaaannaa aaaaaaanac naangntaac nntnccnaaa     300
aa                                                                    302
```

<210> SEQ ID NO 12
<211> LENGTH: 144
<212> TYPE: DNA
<213> ORGANISM: Macaca fascicularis
<220> FEATURE:
<221> NAME/KEY: unsure
<222> LOCATION: 25
<223> OTHER INFORMATION: a or g or c or t, unknown, or other
<220> FEATURE:
<221> NAME/KEY:
<223> OTHER INFORMATION: 700712962H1
<300> PUBLICATION INFORMATION:

<400> SEQUENCE: 12

```
ctcgatgctg ccgggggagg cgggnggagg agacaccagg ggtggccctg agcaccggcg      60
acacctttcc tggactataa attgagcacc tgggatgggt aggggtcaa cgcatcaccg     120
ccgcccgcag tcacagtccg gcca                                            144
```

<210> SEQ ID NO 13
<211> LENGTH: 274
<212> TYPE: DNA
<213> ORGANISM: Macaca fascicularis
<220> FEATURE:
<221> NAME/KEY: unsure
<222> LOCATION: 19, 253
<223> OTHER INFORMATION: a or g or c or t, unknown, or other
<220> FEATURE:
<221> NAME/KEY:
<223> OTHER INFORMATION: 700715135H1
<300> PUBLICATION INFORMATION:

<400> SEQUENCE: 13

```
gacgccaaag ccaggagang ccgcccatcc cgcaggtccg gttctgccag cgagacgaga      60
gttggcgagg gcggaggagt gccgggaatc ccgccacacc ggctatagcc aggccccag     120
cgcgggcctt ggagagagcg tgaaggcggg catcccttg acccggccga ccatccccgt     180
gtctctgcgt ccctgcgctc cagcgcccgc gcggccacca tgatgcaaat ctgcgacacc     240
tacaaccaga agnactcgct ctttaacggc atga                                 274
```

<210> SEQ ID NO 14
<211> LENGTH: 273
<212> TYPE: DNA
<213> ORGANISM: Mus musculus
<220> FEATURE:
<221> NAME/KEY: unsure
<222> LOCATION: 245
<223> OTHER INFORMATION: a or g or c or t, unknown, or other
<220> FEATURE:
<221> NAME/KEY:
<223> OTHER INFORMATION: 701253541H1
<300> PUBLICATION INFORMATION:

<400> SEQUENCE: 14

```
cccgggtaca tgtacagcca ctacgtgctg ctcaagtcca tccgcaatga tatcgagtgg      60
ggagtcctgc accagccttc gtctccgccg gcgggagcg aggagagcac ctggaagccc     120
aaggacatcc tggtgggcct gagtcacttg gagagcgcgg atgcggcgag gaagatctgg     180
agcagcagtt ccactaccac ctgcgcgggc tgcacaccgt gctctccaaa ctcacccgaa     240
aagcnaacat cctcaccatt agatacaagc agg                                  273
```

<210> SEQ ID NO 15
<211> LENGTH: 250
<212> TYPE: DNA
<213> ORGANISM: Mus musculus
<220> FEATURE:
<221> NAME/KEY: unsure
<222> LOCATION: 45
<223> OTHER INFORMATION: a or g or c or t, unknown, or other
<220> FEATURE:
<221> NAME/KEY:
<223> OTHER INFORMATION: 701252210H1
<300> PUBLICATION INFORMATION:

<400> SEQUENCE: 15

```
cttttttgtaa cagtgaccct gtcttaagtc tttcagatct ctttncttg aaacttcgtc      60
gattccattg tgataagcgc acaaacagca ctgttggtaa ccggtactac tttattaatg     120
attttctgtt acactgtaca gtagtcctgt ggcaccctat cccctttcacg ccaccccctcc     180
cccgcccgtg tgtgtaaact ggcgatgtgc cagctaggat gaagcttgcc actcggctag     240
cgaaaataat                                                            250
```

<210> SEQ ID NO 16
<211> LENGTH: 272
<212> TYPE: DNA
<213> ORGANISM: Rattus norvegicus
<220> FEATURE:
<221> NAME/KEY: unsure
<222> LOCATION: 56, 64, 67, 84, 209, 234, 249
<223> OTHER INFORMATION: a or g or c or t, unknown, or other
<220> FEATURE:
<221> NAME/KEY:
<223> OTHER INFORMATION: 700545683H1
<300> PUBLICATION INFORMATION:

<400> SEQUENCE: 16

```
gaccttttat ctgtgctgct ggaggaggta ggaggaggag acatcagggg tggtcntggg      60
gcgnctngga cacctatcct ggantataaa ttgagcacct gggatgcagc aggggggcga     120
agcagccacc atcacccata ctcacagtcc gatcagtgac cgcagcagcg cccttgggca     180
gccaccgtgc cgcaactacg agcactgana accaggggat ttcgcagtgc aagngatcaa     240
ggctagacnc aaccacctac catcctcgtg ag                                   272
```

<210> SEQ ID NO 17
<211> LENGTH: 257
<212> TYPE: DNA
<213> ORGANISM: Rattus norvegicus
<220> FEATURE:
<221> NAME/KEY:
<223> OTHER INFORMATION: 700145292H1
<300> PUBLICATION INFORMATION:

<400> SEQUENCE: 17

```
gcaactcgag cactgagaac caggggattt cgcagtgcaa gagatcaagg ctagacccaa      60
ccacctaaca tcctcgtgag ccaaagctta gcagccgc gcatcaggaa gggctgaact       120
gagacagaag gaagagttag agagggcgga aaggatctg ggaatccagt cacaccggct      180
tcaagcaggc tcccggcatt agcgtttgaa ggcgggcatc gccagaggtc tatctcggtg     240
taccagtgtc cctgtgt                                                    257
```

<210> SEQ ID NO 18
<211> LENGTH: 239
<212> TYPE: DNA
<213> ORGANISM: Rattus norvegicus
<220> FEATURE:
<221> NAME/KEY: unsure
<222> LOCATION: 16, 68
<223> OTHER INFORMATION: a or g or c or t, unknown, or other
<220> FEATURE:
<221> NAME/KEY:
<223> OTHER INFORMATION: 700861443H1
<300> PUBLICATION INFORMATION:

<400> SEQUENCE: 18

```
gacagaagga agagtnagag agggcggaga aggatctggg aatccagtca caccggcttc      60
aagcaggntt cccggcatta gcgtttgaag gcgggcatcg ccagaggtct atctcggtgt     120
accagtgtcc ctgtgtttcc gcgcccgctc ggccaccatg atgcaaatct gcgacacata     180
caaccagaag cactcgctct ttaacgccat gaatcgcttc attggcgcgg tgaacaaca     239
```

<210> SEQ ID NO 19
<211> LENGTH: 302
<212> TYPE: DNA
<213> ORGANISM: Rattus norvegicus
<220> FEATURE:
<221> NAME/KEY:
<223> OTHER INFORMATION: 700225363H1
<300> PUBLICATION INFORMATION:

<400> SEQUENCE: 19

```
gtccctgtgt ttccgcgccc gctcggccac catgatgcaa atctgcgaca catacaacca      60
gaagcactcg ctctttaacg ccatgaatcg cttcattggc gcggtgaaca acatggacca     120
gacggtgatg gtgcccagtc tgctgcgcga tgtaccctg tccgagccgg atctagacaa      180
cgaggtcagc gtggaggtag gcggcagtgg cagctgcctg gaggagcgca cgaccccggc     240
cccaagcccg ggcagcgcca atggaagctt tttcgcgccc tccgggaca tgtacagcca      300
``` ct                                                                      302

<210> SEQ ID NO 20
<211> LENGTH: 286
<212> TYPE: DNA
<213> ORGANISM: Rattus norvegicus
<220> FEATURE:
<221> NAME/KEY: unsure
<222> LOCATION: 62, 283
<223> OTHER INFORMATION: a or g or c or t, unknown, or other
<220> FEATURE:
<221> NAME/KEY:
<223> OTHER INFORMATION: 700643425H1
<300> PUBLICATION INFORMATION:

<400> SEQUENCE: 20
ggaccagacg gtgatggtgc ccagtctgct gcgcgatgta cccctgtccg agccggatct      60
anacaacgag gtcagcgtgg aggtaggcgg cagtggcagc tgcctggagg agcgcacgac     120
cccggcccca agcccgggca cgccaatgg aagcttttc gcgccctccc gggacatgta      180
cagccactac gtgctgctca agtccatccg caacgatatt gagtggggag tcctgcacca     240
gccttcgtcc ccgccggctg ggagtgagga gggcacctgg aanccc                     286

<210> SEQ ID NO 21
<211> LENGTH: 285
<212> TYPE: DNA
<213> ORGANISM: Rattus norvegicus
<220> FEATURE:
<221> NAME/KEY: unsure
<222> LOCATION: 72, 103, 154, 172, 224, 263, 264, 283
<223> OTHER INFORMATION: a or g or c or t, unknown, or other
<220> FEATURE:
<221> NAME/KEY:
<223> OTHER INFORMATION: 700525920H1
<300> PUBLICATION INFORMATION:

<400> SEQUENCE: 21
gtgctgctca agtccatccg caacgatatt gagtggggag tcctgcacca gccttgcgtc      60
cccgccggct gngagtgagg agtggcacct ggaagcccaa ggcatcctg gtgggcctga     120 gccacttgga gagcacggat gcgggcgagg aagntctgga gcagcagttc cnctaccacc     180
tgcgcgggct gcacaccgtg ctctccaaac tcacccgcaa agcnaacatc cttaacaaca     240
gatacaagca ggagatcggc ttnntaatgg gggccattga ggngg                      285

<210> SEQ ID NO 22
<211> LENGTH: 270
<212> TYPE: DNA
<213> ORGANISM: Rattus norvegicus
<220> FEATURE:
<221> NAME/KEY: unsure
<222> LOCATION: 87
<223> OTHER INFORMATION: a or g or c or t, unknown, or other
<220> FEATURE:
<221> NAME/KEY:
<223> OTHER INFORMATION: 700773927H1
<300> PUBLICATION INFORMATION:

<400> SEQUENCE: 22
ggccaacatc cttaccaaca gatacaagca ggagatcggc ttcagtaatt ggggccactg      60
aggcggggtt gtccccgctg cccagcncc tctcggtcg gctctaccac ccccctctct      120
ttcctccaaa ctattttctt cctggttgtg gggcgcgaag ggcacgctgt aaagttgggc     180
tgtgtacttg gtggggtttg tgtggagaaa acagagcaga gagcagagga aatatcgcca     240
gagagggggg ttcaaagacc cccggagggc                                       270

```
<210> SEQ ID NO 23
<211> LENGTH: 283
<212> TYPE: DNA
<213> ORGANISM: Rattus norvegicus
<220> FEATURE:
<221> NAME/KEY:
<223> OTHER INFORMATION: 700513679H1
<300> PUBLICATION INFORMATION:

<400> SEQUENCE: 23
ggaactgggc cgatgtcctt cattcagcct gtgcctttct tggggtttct tttctctttt      60
tctttccgga agagaagggc ctgagaaagg gccatgccag ggcacagcgc tgggttgcca     120
cacttgggag ggcagcttct agctgggtgc tcggggagg cggggcacag cctcctgccc      180
gccctgcttt gagctgcaag aggaggcctt ggcgttgcta ggattgcgtc agttttcctg     240
tttgcactat ttcttttgt aacagtgacc ctgtcttaag tat                        283

<210> SEQ ID NO 24
<211> LENGTH: 266
<212> TYPE: DNA
<213> ORGANISM: Rattus norvegicus
<220> FEATURE:
<221> NAME/KEY:
<223> OTHER INFORMATION: 700767486H1
<300> PUBLICATION INFORMATION:

<400> SEQUENCE: 24
tttcagatct ttttgctttg aaacttcgtc gattccattg tgataagcgc acaagcagca      60
ctgttggtaa ccggtactac tttattaatg attttctgtt acactgtaca gtagtcctat     120
ggcaccccat cccttcacg ccacccctcc cccacccgt gtgtgtaaac tggtgacgtg       180
ccagctagga tgaagcttgc cactcggcca gcgaaaataa taacattatt gtgagaaagt     240
ggatttatct aaagtggaac caactg                                          266

<210> SEQ ID NO 25
<211> LENGTH: 199
<212> TYPE: DNA
<213> ORGANISM: Rattus norvegicus
<220> FEATURE:
<221> NAME/KEY: unsure
<222> LOCATION: 8, 36, 40
<223> OTHER INFORMATION: a or g or c or t, unknown, or other
<220> FEATURE:
<221> NAME/KEY:
<223> OTHER INFORMATION: 700327166H1
<300> PUBLICATION INFORMATION:

<400> SEQUENCE: 25
agccactngg ccagcgaaaa taataacatt attgtnagan agtggattta tctaatggaa      60
ccaactgaca ttctatctgt gttgtacgta gaatgatgaa gggctccact gttgttatat     120
gtcttgttta tttaaaactt ttttttaatc cagatgtaga ctatattcta aaaataaaa      180 gctcagatgt gttaaccac                                                  199

<210> SEQ ID NO 26
<211> LENGTH: 152
<212> TYPE: PRT
<213> ORGANISM: Danio rerio
<220> FEATURE:
<221> NAME/KEY:
<223> OTHER INFORMATION: g861207
<300> PUBLICATION INFORMATION:
```

```
<400> SEQUENCE: 26

Met Gln Met Ser Glu Pro Leu Ser Gln Lys Asn Ala Leu Tyr Thr
 1               5                  10                  15

Ala Met Asn Arg Phe Leu Gly Ala Val Asn Asn Met Asp Gln Thr
                20                  25                  30

Val Met Val Pro Ser Leu Leu Arg Asp Val Pro Leu Asp Gln Glu
                35                  40                  45

Lys Glu Gln Gln Lys Leu Thr Asn Asp Pro Gly Ser Tyr Leu Arg
                50                  55                  60

Glu Ala Glu Ala Asp Met Tyr Ser Tyr Tyr Ser Gln Leu Lys Ser
                65                  70                  75

Ile Arg Asn Asn Ile Glu Trp Gly Val Ile Arg Ser Glu Asp Gln
                80                  85                  90

Arg Arg Lys Lys Asp Thr Ser Ala Ser Glu Pro Val Arg Thr Glu
                95                  100                 105

Glu Glu Ser Asp Met Asp Leu Glu Gln Leu Leu Gln Phe His Leu
                110                 115                 120

Lys Gly Leu His Gly Val Leu Ser Gln Leu Thr Ser Gln Ala Asn
                125                 130                 135

Asn Leu Thr Asn Arg Tyr Lys Gln Glu Ile Gly Ile Ser Gly Trp
                140                 145                 150

Gly Gln

<210> SEQ ID NO 27
<211> LENGTH: 150
<212> TYPE: PRT
<213> ORGANISM: Mus musculus
<220> FEATURE:
<221> NAME/KEY:
<223> OTHER INFORMATION: g1171574
<300> PUBLICATION INFORMATION:

<400> SEQUENCE: 27

Met Gln Val Leu Thr Lys Arg Tyr Pro Lys Asn Cys Leu Leu Thr
 1               5                  10                  15

Val Met Asp Arg Tyr Ser Ala Val Val Arg Asn Met Glu Gln Val
                20                  25                  30

Val Met Ile Pro Ser Leu Leu Arg Asp Val Gln Leu Ser Gly Pro
                35                  40                  45

Gly Gly Ser Val Gln Asp Gly Ala Pro Asp Leu Tyr Thr Tyr Phe
                50                  55                  60

Thr Met Leu Lys Ser Ile Cys Val Glu Val Asp His Gly Leu Leu
                65                  70                  75

Pro Arg Glu Glu Trp Gln Ala Lys Val Ala Gly Asn Glu Thr Ser
                80                  85                  90

Glu Ala Glu Asn Asp Ala Ala Glu Thr Glu Glu Ala Glu Glu Asp
                95                  100                 105

Arg Ile Ser Glu Glu Leu Asp Leu Glu Ala Gln Phe His Leu His
                110                 115                 120

Phe Cys Ser Leu His His Ile Leu Thr His Leu Thr Arg Lys Ala
                125                 130                 135

Gln Glu Val Thr Arg Lys Tyr Gln Glu Met Thr Gly Gln Val Leu
                140                 145                 150
```